US011399618B2

United States Patent
Farran et al.

(10) Patent No.: US 11,399,618 B2
(45) Date of Patent: Aug. 2, 2022

(54) METHODS AND APPLICATORS FOR APPLYING SKIN-TIGHTENING FILM PRODUCTS

(71) Applicant: L'Oreal, Paris (FR)

(72) Inventors: Alexandra Jane Elisa Farran, Dayton, NJ (US); Anne-Laure Bernard, New York, NY (US); Theresa Phamduy, Jersey City, NJ (US); William Bickford, Clark, NJ (US); Olivier Dovergne, Saint-Ouen (FR)

(73) Assignee: L'Oreal, Paris (FR)

( * ) Notice: Subject to any disclaimer, the term of this patent is extended or adjusted under 35 U.S.C. 154(b) by 358 days.

(21) Appl. No.: 15/965,647

(22) Filed: Apr. 27, 2018

(65) Prior Publication Data
US 2019/0328111 A1 Oct. 31, 2019

(51) Int. Cl.
*A45D 40/26* (2006.01)
*A45D 34/04* (2006.01)
(Continued)

(52) U.S. Cl.
CPC ......... *A45D 40/261* (2013.01); *A45D 34/041* (2013.01); *A61K 8/0204* (2013.01);
(Continued)

(58) Field of Classification Search
CPC .. A45D 40/0087; A45D 40/26; A45D 40/261; A45D 40/28; A45D 34/04; A45D 34/041; A45D 2200/10; A45D 2200/1009; A45D 2200/1018; A45D 2200/1036; A45D 2200/1045; A45D 2200/1063;
(Continued)

(56) References Cited

U.S. PATENT DOCUMENTS 6,315,482 B1 * 11/2001 Girardot ................ A45D 40/00
15/104.93
6,336,763 B1 * 1/2002 Losier .................... A45D 40/04
401/205
(Continued)

FOREIGN PATENT DOCUMENTS

CN 104523478 4/2015
EP 0 839 009 A1 5/1998
(Continued)

OTHER PUBLICATIONS

Emma. "What Is Matrixyl? Aging Skin Wants to Know." SkincareRX, Thehut.com LTD, Sep. 28, 2018, www.skincarerx.com/blog/ingredients/matrixyl-aging-skin-wants-know/. (Year: 2018).*
(Continued)

*Primary Examiner* — Rachel R Steitz
*Assistant Examiner* — Karim Asqiriba
(74) *Attorney, Agent, or Firm* — Christensen O'Connor Johnson Kindness PLLC

(57) ABSTRACT

A stencil or stamp applicator is used for applying a skin-tightening composition onto skin surfaces. The composition applied with a stencil or stamp results in a discontinuous film made up of sections of about 20 to 150 microns. The discontinuity of the film results in more comfort and a more natural look of facial movement while still retaining a good skin-tightening effect.

10 Claims, 16 Drawing Sheets

(51) Int. Cl.
*A61K 8/81* (2006.01)
*A61K 8/898* (2006.01)
*A61K 8/02* (2006.01)
*A61Q 19/00* (2006.01)
*A61K 8/92* (2006.01)

(52) U.S. Cl.
CPC ............ *A61K 8/8147* (2013.01); *A61K 8/898* (2013.01); *A61K 8/92* (2013.01); *A61Q 19/00* (2013.01); *A45D 2200/10* (2013.01); *A45D 2200/25* (2013.01); *A61K 2800/87* (2013.01)

(58) Field of Classification Search
CPC ...... A45D 2200/25; A61K 8/89; A61K 8/898; A61K 8/899; A61Q 19/00; A61Q 19/08; B05C 9/025; B05C 17/04; B05C 17/06; B05C 17/08
USPC ........ 132/317, 319, 320, 333; 401/261, 265, 401/266; 15/104.93; 118/213, 301
See application file for complete search history.

(56) References Cited

U.S. PATENT DOCUMENTS

| | | | |
|---|---|---|---|
| 6,558,682 B2 | 5/2003 | Yen et al. | |
| 8,277,791 B2 | 10/2012 | Zheng | |
| 9,050,474 B2 | 6/2015 | Sandstrom | |
| 2007/0224158 A1 | 9/2007 | Cassin et al. | |
| 2009/0032054 A1* | 2/2009 | Griffiths | A45D 33/38 132/320 |
| 2009/0197054 A1* | 8/2009 | Chauhan | B41M 3/00 428/195.1 |
| 2011/0076448 A1* | 3/2011 | Agarwal | G03F 7/0388 428/138 |
| 2011/0129956 A1* | 6/2011 | Polito | H01L 31/02363 438/71 |
| 2011/0280647 A1* | 11/2011 | Wilson | A45D 34/041 401/208 |
| 2014/0286687 A1* | 9/2014 | Van Alphen | A45D 40/24 401/49 |
| 2016/0128912 A1* | 5/2016 | McConaughy | A61K 8/87 510/140 |
| 2017/0216185 A1 | 8/2017 | Schultze et al. | |

FOREIGN PATENT DOCUMENTS

| | | | |
|---|---|---|---|
| EP | 1 204 397 A1 | 5/2002 | |
| EP | 1 204 399 A2 | 5/2002 | |
| WO | 2016/100690 A1 | 6/2016 | |
| WO | 2016100742 A1 | 6/2016 | |
| WO | WO-2016100690 A1 * | 6/2016 | ............... A61K 8/29 |
| WO | 2015147054 A1 | 4/2017 | |

OTHER PUBLICATIONS

Cartlidge, Edwin. "New State of Matter Seen in Clay." Science, AAAS, Dec. 21, 2010, www.sciencemag.org/news/2010/12/new-state-matter-seen-clay#:~:text=A%20gel%20is%20a%20liquid,pharmaceuticals%20to%20paints%20and%20cosmetics. (Year: 2010).*

Etsy, QuirkyCraftsShop, "Diamond Nail Stencils, Geometric Nail Stencil, DIY Nails," <https://www.etsy.com/fr/listing/289751065/diamant-a-ongles-pochoirs-pochoir-ongles >, available as early as Oct. 18, 2017, retrieved Apr. 27, 2018, 4 pages.

Bing, Diamond Stencil Template—Bing Images, <https://www.bing.com/images/search?q=Diamond+Stencil+Template&FORM=IDINTS>, available as early as Oct. 18, 2017, retrieved Apr. 30, 2018, 1 page.

* cited by examiner

METHODS AND APPLICATORS FOR APPLYING SKIN-TIGHTENING FILM PRODUCTS

SUMMARY

In an embodiment, a combination comprises a skin-tightening composition and an applicator configured to apply the skin-tightening composition in a discontinuous manner, wherein the applicator comprises an application surface having a plurality of first discontinuous subsurfaces separated by a continuous second subsurface, where the plurality of discontinuous subsurfaces are arranged in a repeating pattern; and a skin-tightening composition.

In an embodiment, the first subsurfaces are open spaces and the second subsurface forms ribs or strips between the open spaces.

In an embodiment, the open spaces have a non-isometric shape in the length and width dimensions.

In an embodiment, the open spaces have diamond, square, rectangular, or any other polygon shape in the length and width dimension.

In an embodiment, the open spaces have more than one shape.

In an embodiment, the open spaces have more than one size.

In an embodiment, the skin-tightening composition is provided in a container, and the applicator and skin-tightening composition are provided as a unit.

In an embodiment, the skin-tightening composition is selected from the group consisting of: anionic copolymers based on methacrylic acid and methyl methacrylate in a random, block, or alternating configuration, organopolysiloxanes, silicone-urethane copolymers, ethylenically unsaturated polycarbosiloxanes, silicone-urethane copolymers and an elastomer, an elastomer, an adhesive polymer, and a filler, and wax microparticles In an embodiment, the combination comprises a stencil including a material having a first and second major surface forming opposite sides of the material, wherein the first and second surfaces are separated by a thickness of the material with open spaces in the material that traverse the material from the first major surface to the second major surface, wherein a majority of the open spaces have a similar shape to create a repeating pattern of open spaces along a length dimension and a width dimension of the material, and wherein the maximum average size of an open space in either a length dimension or width dimension is from 20 microns to 150 microns.

In an embodiment, the stencil is a sheet or a mesh of filaments.

In an embodiment, the stencil has an adhesive on one of the first or second major surfaces.

In an embodiment, the stencil has a backing sheet to which the stencil is adhered.

In an embodiment, the first subsurfaces are protrusions and the second subsurface forms grooves in between the first subsurfaces.

In an embodiment, outward facing surfaces of the distal ends of the protrusions have a non-isometric shape in the length and width dimensions.

In an embodiment, outward facing surfaces of the distal ends of the protrusions have a diamond, square, rectangular, or any other polygon shape in the length and width dimension.

In an embodiment, outward facing surfaces of the distal ends of the protrusions include more than one shape of outward facing surface.

In an embodiment, outward facing surfaces of the distal ends of the protrusions include more than one size of outward facing surfaces.

In an embodiment, outward facing surfaces of the distal ends of the protrusions lie along a planar surface.

In an embodiment, outward facing surfaces of the distal ends of the protrusions lie on a roller.

In an embodiment, outward facing surfaces of the distal ends of the protrusions collectively lie on a convex surface.

In an embodiment, outward facing surfaces of the distal ends of the protrusions lie on a convex surface curving upwards from a center in all dimensions.

In an embodiment, outward facing surfaces of the distal ends of the protrusions are flat.

In an embodiment, the combination comprises a stamp having protrusions extending from at least one surface, wherein outward facing surfaces of the protrusions collectively form a surface for stamping, a majority of the outward facing surfaces of the distal ends of the protrusions have a similar shape to create a repeating pattern along a length dimension and a width dimension, and wherein the maximum average size of the outward facing surface area of the distal ends of the protrusions in either a length dimension or width dimension is from 20 microns to 150 microns.

In an embodiment, a method of applying a skin-tightening composition comprises placing a stencil on a skin area, wherein the stencil includes a material having a first and second major surface forming opposite sides of the material, wherein the first and second surfaces are separated by a thickness of the material with open spaces in the material that traverse the material from the first major surface to the second major surface, wherein a majority of the open spaces have a similar shape to create a repeating pattern of open spaces along a length dimension and a width dimension of the material, and wherein the maximum average size of an open space in either a length dimension or width dimension is from 20 microns to 150 microns; applying a skin-tightening composition to the stencil while on the skin area; and removing the stencil from the skin area that leaves a patterned skin-tightening composition on the skin area.

In an embodiment, a method of applying a skin-tightening composition comprises providing a stamp having protrusions extending from at least one surface, wherein outward facing surfaces of the protrusions collectively form a surface for stamping, a majority of the outward facing surfaces of the distal ends of the protrusions have a similar shape to create a repeating pattern along a length dimension and a width dimension, and wherein the maximum average size of the outward facing surface area of the distal ends of the protrusions in either a length dimension or width dimension is from 20 microns to 150 microns; applying a skin-tightening composition at least on the outward facing surfaces of the protrusions and bringing the skin-tightening composition on the stamp in contact with a skin area; and withdrawing the stamp and leaving a patterned skin-tightening composition on the skin area.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Skin-tightening polymeric film forming products are very effective at reducing the appearance of wrinkles and bags on the face and also on reducing sagging skin generally. However, some products can cause discomfort on the face and produce an unnatural look upon facial movement. Accordingly, this disclosure relates to applicators and methods for applying skin-tightening products that give more flexibility for the skin to move.

Embodiments include a method and an applicator to apply skin-tightening film products on, for example, the face by generating a discontinuous film on the skin to provide more comfort and a more natural look of facial movement while retaining a good skin-tightening effect. Embodiments of applicators include a stamp or a stencil designed respectively with a continuous pattern such as a grid, or a discontinuous pattern with a non-isotropic shapes such as a diamond with which the skin-tightening film composition is applied on the skin.

In one embodiment, the composition is deposited on a patterned stamp. The composition is transferred onto the skin following the stamp pattern by pressing the stamp on the skin. In a second embodiment, a patterned stencil is applied onto the skin. The composition is then applied over the patterned stencil like in screen printing techniques. Then, the stencil is removed, leaving the composition on skin following the negative pattern of the stencil.

Embodiments include application of a variety of skin care compositions, including, but not limited to: organic solvent based films containing polymeric elastomer, water based films containing polymeric elastomers, such as are available under the designation BAYCUSAN®, water based films containing high MW water soluble polymers, for example, pullulan and carrageenan.

Embodiments of film compositions applied to skin with the stencil or stamp applicators provide more comfortable wear with good tightening effect (fine line and bag appearance reduction), and a more natural look upon facial movement, such as smiling.

The Applicators

Applicators of skin-tightening compositions include stencils and stamps.

Figure 1A:
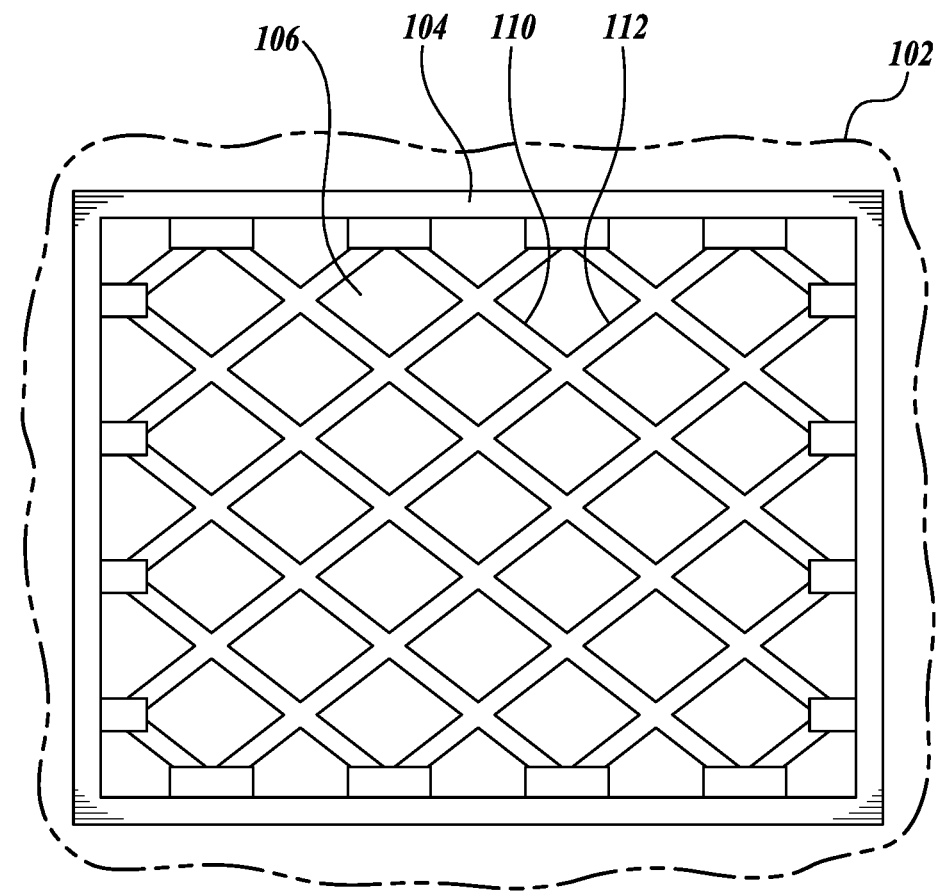
FIG. 1A is a diagrammatical illustration of a stencil applicator and a step of a method according to an embodiment.

FIG. 1A is a diagrammatical illustration of an embodiment of a stencil 104 and a step of a method for applying a skin-tightening film to a skin surface via the use of a stencil. FIG. 1A shows the application of the stencil 104 onto a skin surface 102, such as on the face.

In an embodiment, the stencil 104 has an application surface having a plurality of first discontinuous subsurfaces as open holes 106 separated by a continuous second subsurface of ribs or strips 110, where the plurality of discontinuous subsurfaces are arranged in a repeating pattern.

In an embodiment, a stencil 104 is made from a thin sheet of material. In an embodiment, the sheet material is flexible. The stencil 104 is provided in various sizes. In an embodiment, each stencil 104 can be several centimeters in both length and width. In an embodiment, the outer boundary outline of the stencil 104 is a simple polygon, such as a square or rectangle. In an embodiment, the outer boundary outline of the stencil 104 includes curves and resembles a "kidney" shape. The thickness of the sheet material is not particularly limiting. In an embodiment, the sheet material is thin enough to be flexible, while also resistant to tearing. Suitable materials include plastics, elastomers, papers, fabrics, or metals.

Figure 1B:
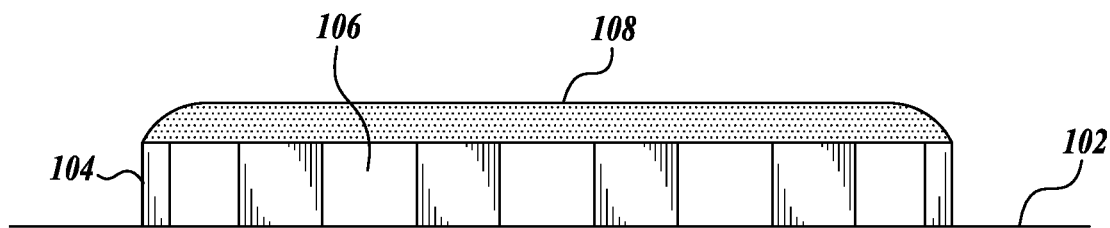
FIG. 1B is a diagrammatical illustration of a stencil applicator and a step of a method according to an embodiment.

The stencil 104 includes open spaces 106 that traverse the stencil 104 from a first major surface to a second major surface as best seen in FIG. 1B. In the stencil 104, a majority of the open spaces 106 have a similar shape to create a repeating pattern of open spaces 106 along a length dimension and a width dimension of the stencil 104. In an embodiment, the maximum average size of an open space 106 in either a length dimension or width dimension is from 20 microns to 150 microns. In the FIGURES, the open spaces are not drawn to any scale, but, are enlarged to show the non-isometric shapes of the openings 106. In an embodiment of the stencil 104, all of the open spaces 106 have a similar shape to create a repeating pattern of open spaces along a length dimension and a width dimension of the stencil 104. In an embodiment of the stencil 104, only a majority of the open spaces 106 have a similar shape.

In the stencil 104, each open space 106 is surrounded by material. In an embodiment, the open spaces 106 are completely surrounded by material. In the embodiment of the stencil of FIG. 1A, the pattern of open spaces 106 is created by thin strips of material 110, 112 in a crossing pattern at angles other than 90 degrees. Each open space 106 can be separated from the adjacent open spaces by not more than from 1 to 130 microns, for example. That is, the material strips 110, 112 surrounding each open space 106 are on the order of 1 to 130 microns wide. In an embodiment, open spaces 106 are not connected to adjacent open spaces.

Referring to FIG. 1B, a subsequent step of a method wherein the stencil 104 is used in applying a film composition 108 onto a skin surface 102 is illustrated. The stencil 104 from FIG. 1A has been placed onto the skin surface 102, and the film composition 108 is applied on the upper side of the stencil 104. A spatula or any straight edge is used to push the film composition 108 through the open spaces 106 in the stencil 104 to reach the skin surface 102.

Figure 1C:
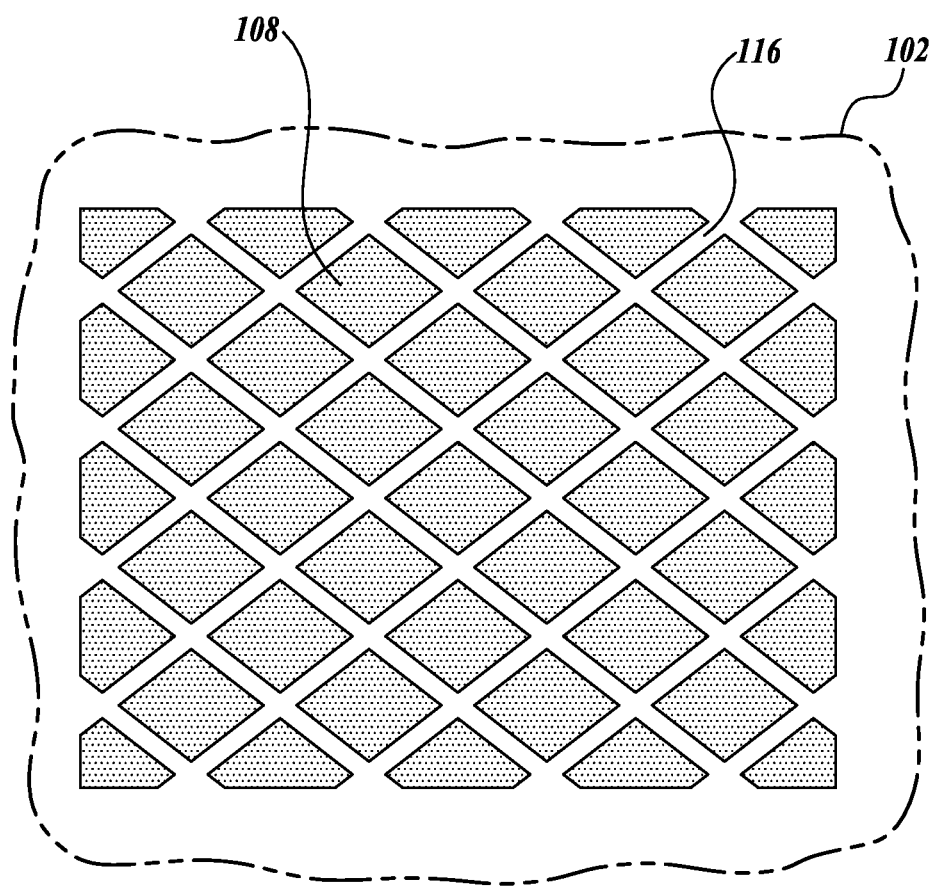
FIG. 1C is a diagrammatical illustration of a discontinuous film and a step of a method according to an embodiment.

Referring to FIG. 1C, after the film composition has been applied as described and illustrated in FIG. 1B, the stencil 104 is removed from the skin surface 102, which leaves the film composition 108 in the pattern corresponding to the open spaces 106 of the stencil 104. Depending on the nature of the film composition, the stencil 104 is removed immediately or a period of time is allowed for curing of the film composition. The use of a stencil 104 as herein described for applying a composition on a skin surface, results in a discontinuous film composition.

A discontinuous film composition as shown in FIG. 1C includes a plurality of individual micron-sized film sections 108 covering an area of skin surface 102 that corresponds approximately with the open spaces 106 of the stencil. In an embodiment, the maximum average size of individual film sections 108 in either the width or the length dimension is from 20 to 150 microns. In an embodiment, the size of individual film sections 108 in either the width or length dimension is any value from 20 to 150, including, but not limited to 20, 25, 30, 35, 40, 45, 50, 55, 60, 65, 70, 75, 80, 85, 90, 95, 100, 105, 110, 115, 120, 125, and 130, or any range of any two values as endpoints. In an embodiment, the separation space 116 between any two individual film sections is from 1 to 130 microns or any value within such range.

While a representative stencil is illustrated in FIGS. 1A to 1C, stencils are not particularly limiting. Stencils include open spaces, the sum of which defines a negative space, and positive space (not open space). In an embodiment, the combined open spaces 106 have a total area that is on the order of at least 100% of the positive area of any stencil. In an embodiment, the open (negative) area of any stencil is a majority of the surface area of the major side of the stencil. In an embodiment, the open (negative) area of any stencil is from 50% to 99% of the total surface area (open and positive space) of the major side of any stencil.

In an embodiment, a stencil is made from a continuous sheet material, wherein the open spaces 106 are then created in the material through the process of microperforation or microcutting. In an embodiment, a stencil has an adhesive on a major surface side. In an embodiment, a plurality of stencils with an adhesive on a major surface side are provided on a backing sheet. In an embodiment, a plurality of stencils are provided in a single sheet or in a tape. Where stencils come adhered to a backing sheet, microcuts are provided deep enough to cut through the stencil material but leave the backing material uncut. In the embodiment, the open spaces are left filled with the sheet material until the stencils are lifted from the backing sheet. This leaves the cut material on the backing sheet, and the adhesive backed stencil with the open spaces is applied the skin surface, the adhesive providing a secure hold of stencil to skin. In an embodiment, a stencil is made by creating a mesh of fibers or wires, such that open spaces are created in the mesh. Extruded or melt spun plastic fiber is laid down in a criss-cross pattern such that the fibers are allowed to bond to one another. The mesh is cut to a desired shape.

In an embodiment, open spaces in any stencil have a non-isometric shape or outline in the length and width dimensions. That is, in an embodiment, the open spaces are not circles. In an embodiment, the open spaces of any stencil have diamond, square, rectangular, or any other polygon shape in the length and width dimension. In an embodiment, open spaces in any stencil are a combination of curves with straight lines. In an embodiment, open spaces in any stencil are made from curves.

Figure 2A:
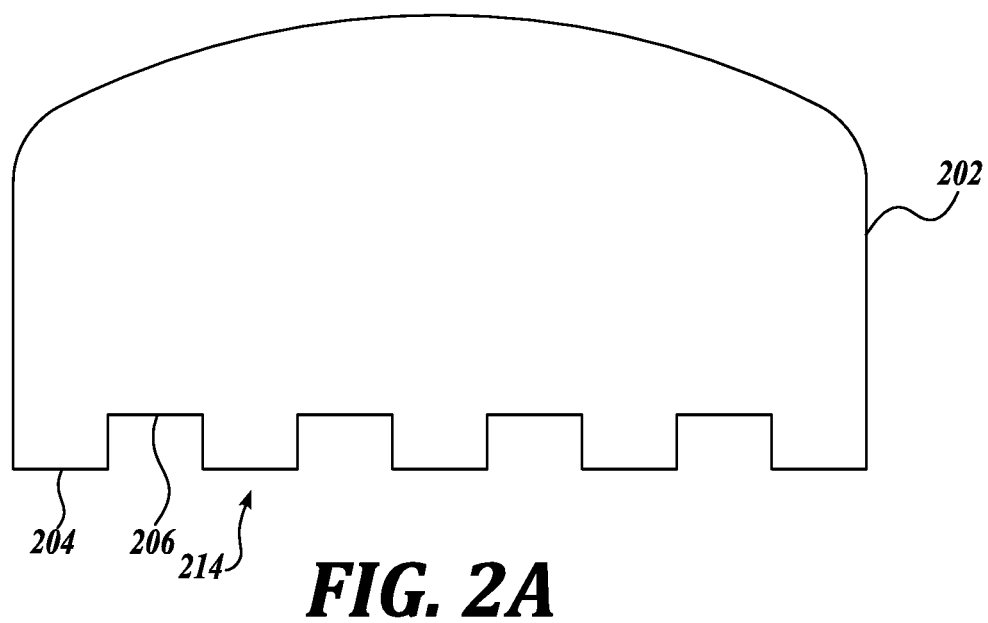
FIG. 2A is a diagrammatical illustration of a stamp applicator and a step of a method according to an embodiment.

FIG. 2A is a diagrammatical illustration of an embodiment of a stamp 202 for applying a skin-tightening film to a skin surface via the use of the stamp 202.

In an embodiment, a stamp 202 is made from a unitary or monolithic material. Material for stamps include plastics, rubbers, elastomers, paper, metal, or any combination thereof. In an embodiment, a stamp 202 is made from more than one component assembled together. In an embodiment, the stamp 202 has an application surface having a plurality of first discontinuous subsurfaces as protrusions 204 separated by a continuous second subsurface of grooves 206, where the plurality of discontinuous subsurfaces are arranged in a repeating pattern.

In an embodiment, the stamp 202 includes at least one side 214 having protrusions 204 used for stamping. In an embodiment, the side 214 used for stamping (or the stamping side 214) is several centimeters in both length and width. However, the size of the side 214 used for stamping varies. In an embodiment, the side 214 used for stamping is flat or planar. In an embodiment, the side 214 used for stamping is non-planar. In an embodiment, the side 214 used for stamping includes concave surfaces, convex surfaces, or a combination of surfaces. The proximal ends of the protrusions 204 lie on or are attached to the underlying surface or grooves 206. In an embodiment, protrusions 204 from the surface grooves 206 project normal to the surface 206. In an embodiment, protrusions 204 extending from the surface grooves 206 have a similar length. The length of the protrusions 204 is not particularly limiting. However, the length of protrusions 204 is generally smaller than either the length or the width dimension of the outward facing surfaces of the distal ends of the protrusions 204. When protrusions 204 of similar length are formed or otherwise added to the surface 206, the distal ends of the protrusions 204 will collectively lie on an imaginary surface resembling the underlying surface 206. That is, if protrusions 204 are provided on a planar surface, the distal ends of the protrusions 204 will lie on a plane. If the protrusions 204 are provided on a curved surface, the distal ends of the protrusions 204 will lie on a curved surface. The outward-facing surfaces of the distal ends of the protrusions 204 collectively form the area of surface used for stamping. The protrusions 204 are provided on the side 214 along both the width and length dimensions and create a repeating pattern over an area. In an embodiment, a majority of the outward facing surfaces of the distal ends of protrusions 204 have a similar shape with respect to the length and width dimensions. In an embodiment, all of the outward facing surfaces of the distal ends of the protrusions 204 have a similar shape.

In an embodiment, the maximum average size of the outward facing surface of a protrusion 204 in either a length dimension or width dimension is from 20 microns to 150 microns. In the FIGURES, the protrusions are not drawn to any scale. In the stamp 202, the protrusions 204 are surrounded by open spaces in both the length and width dimension, meaning that each protrusion 204 is discrete. Each protrusion 204 can be separated from the adjacent protrusions by a space of not more than from 1 to 130 microns, for example.

Figure 2B:
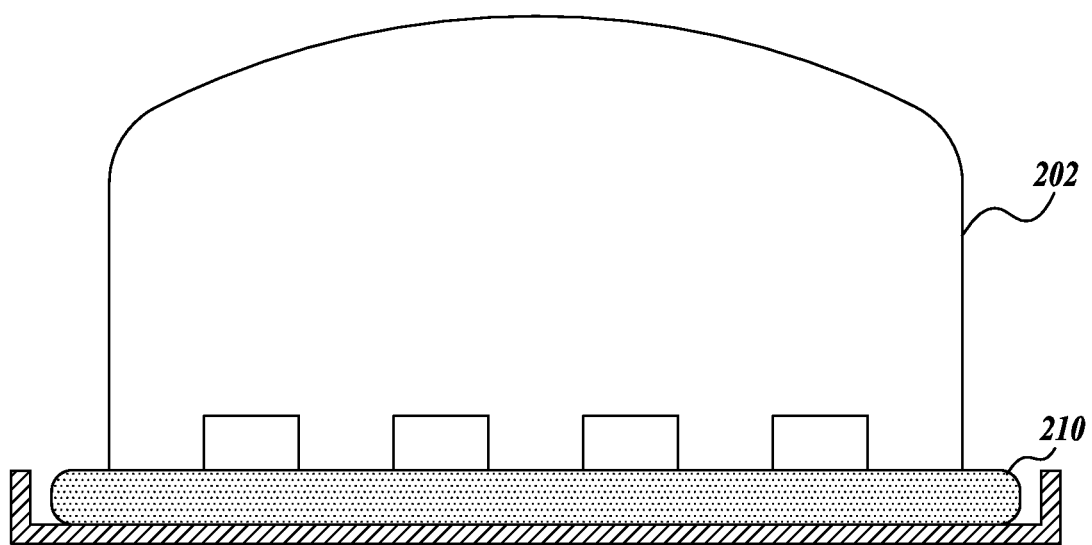
FIG. 2B is a diagrammatical illustration of a stamp applicator and a step of a method according to an embodiment.

Referring to FIG. 2B, a subsequent step of a method wherein the stamp 202 is used in applying a film composition 210 onto a skin surface is illustrated. The stamp 202 from FIG. 2A is loaded with a film composition 210 on the stamping side 214 of the stamp 202. That is, the outward facing distal ends of protrusions 204 are loaded with film composition 210. The stamp 202 can be loaded with film composition, for example, by pressing against a pad wetted with the film composition or dipped in a container of the film composition.

Figure 2C:
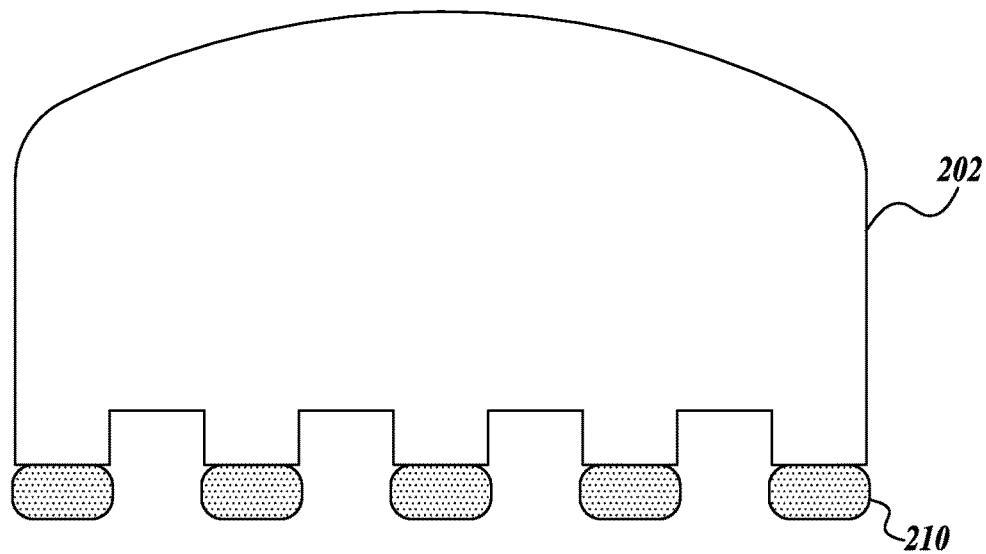
FIG. 2C is a diagrammatical illustration of a stamp applicator and a step of a method according to an embodiment.

After pressing the stamp 202 onto the pad or container as in FIG. 2B, the stamp 202 is removed and will be loaded with film composition primarily on the outward facing distal ends of the protrusions 204 as shown in FIG. 2C. In the case where film composition can bridge across two or more protrusions, the spacing between protrusions is increased to avoid bridging, as a purpose of the stamp 202 is to create a discontinuous film.

Figure 2D:
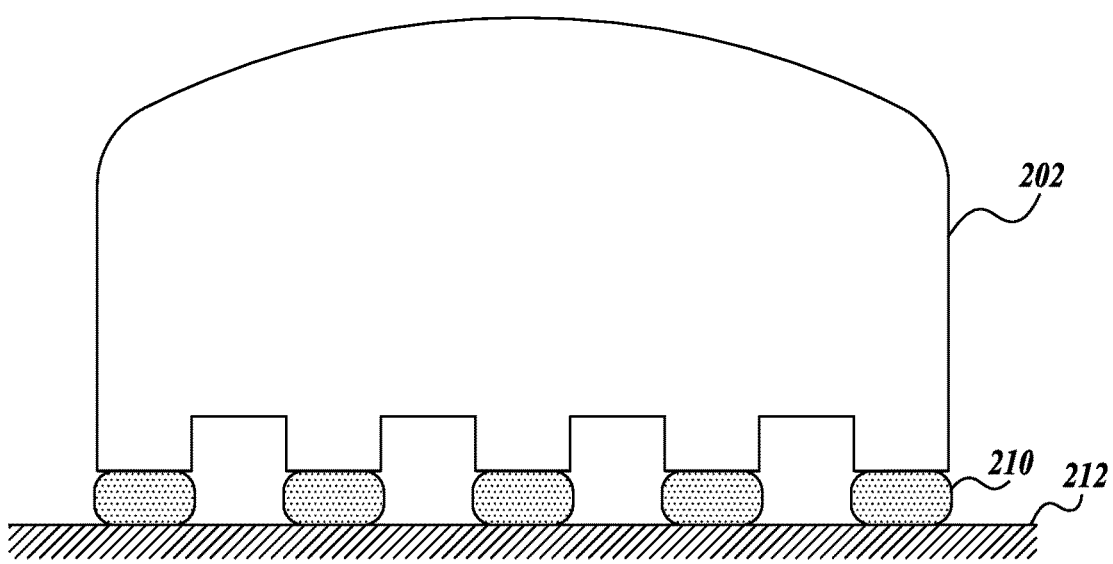
FIG. 2D is a diagrammatical illustration of a stamp applicator and a step of a method according to an embodiment.
Figure 2E:
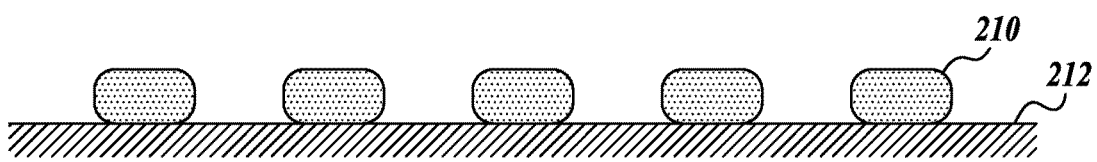
FIG. 2E is a diagrammatical illustration of a discontinuous film and a step of a method according to an embodiment.

Next in FIG. 2D, the stamp 202 from FIG. 2C is pressed against a skin surface 212, thus transferring the film composition from the outward facing distal ends of the protrusions onto the skin surface 212 as in FIG. 2E in the pattern corresponding to the outward facing distal ends of protrusions 204.

Figure 2F:
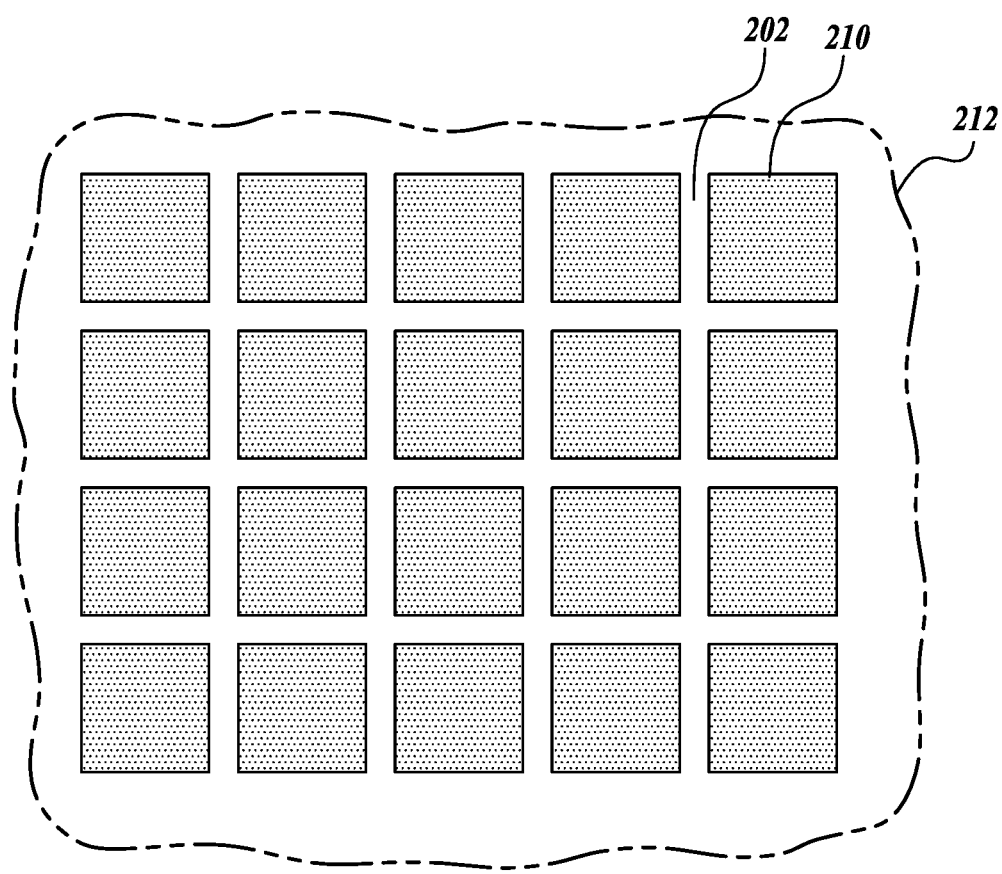
FIG. 2F is a diagrammatical illustration of a discontinuous film and a step of a method according to an embodiment.

The use of a stamp 202 as herein described for applying a composition on a skin surface, results in a discontinuous film composition. A discontinuous film composition as shown in FIG. 2F includes a plurality of individual discrete micron-sized sections 210 covering an area of skin surface 212 corresponding approximately to the area of the stamping side 214 area. In an embodiment, the maximum average size of individual film sections 210 in either the width or the length dimension is from 20 to 150 microns. In an embodiment, the size of individual film sections 108 in either the width or length dimension is any value from 20 to 150, including, but not limited to 20, 25, 30, 35, 40, 45, 50, 55, 60, 65, 70, 75, 80, 85, 90, 95, 100, 105, 110, 115, 120, 125, and 130, or any range of any two values as endpoints. In an embodiment, the separation space 202 between any two individual film sections 210 is from 1 to 130 microns or any value within such range.

In an embodiment, the combined surface area of the outward facing distal ends of protrusions 204 have a total area that is on the order of at least 100% of the open areas of the stamping side 214. That is, the stamping side 214 area has a total area that is made up of 50% protrusions and 50% open space. In an embodiment, the area composed of the outward facing distal ends of protrusions 204 is a majority of the stamping side 214 area. In an embodiment, the area composed of the outward facing distal ends of protrusions 204 is from 50% to 99% of the total area (open and positive space) of the stamping side 214.

In an embodiment, the outward facing surface area of the distal end of a protrusion 204 is a non-isometric shape or outline in the length and width dimensions. That is, in an embodiment, the outward facing surface area shape of the distal end of a protrusion 204 is not circular. In an embodiment, the outward facing distal surface area shape of the distal end of a protrusion 204 is a diamond, square, rectangular, or any other polygon shape in the length and width dimension. In an embodiment, the outward facing surface area of the distal end of a protrusion 204 is a combination of curves with straight lines. In an embodiment, the outward facing surface area of the distal end of a protrusion 204 is made from curves without straight lines.

Figure 3A:
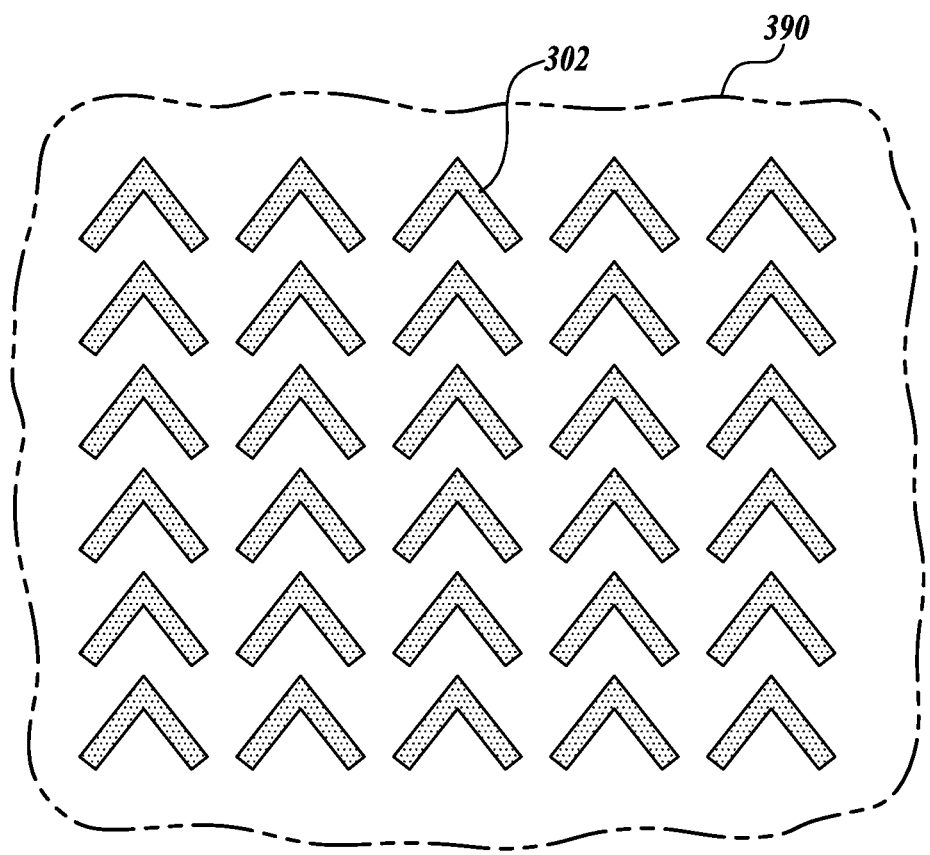
FIG. 3A is a diagrammatical illustration of a discontinuous film.

The open space shapes of stencils and the distal end shapes of protrusions of stamps are not limited. Many shapes are possible for the open spaces of stencils and the distal ends for protrusions of stamps FIG. 3A is a diagrammatical illustration of a discontinuous film composition having similar discrete micron sized film sections 302 spaced apart and not touching each other that cover an area on the skin surface 390 made using either a stencil or stamp. The film sections 302 are a polygon shape of multiple straight sides.

Figure 3B:
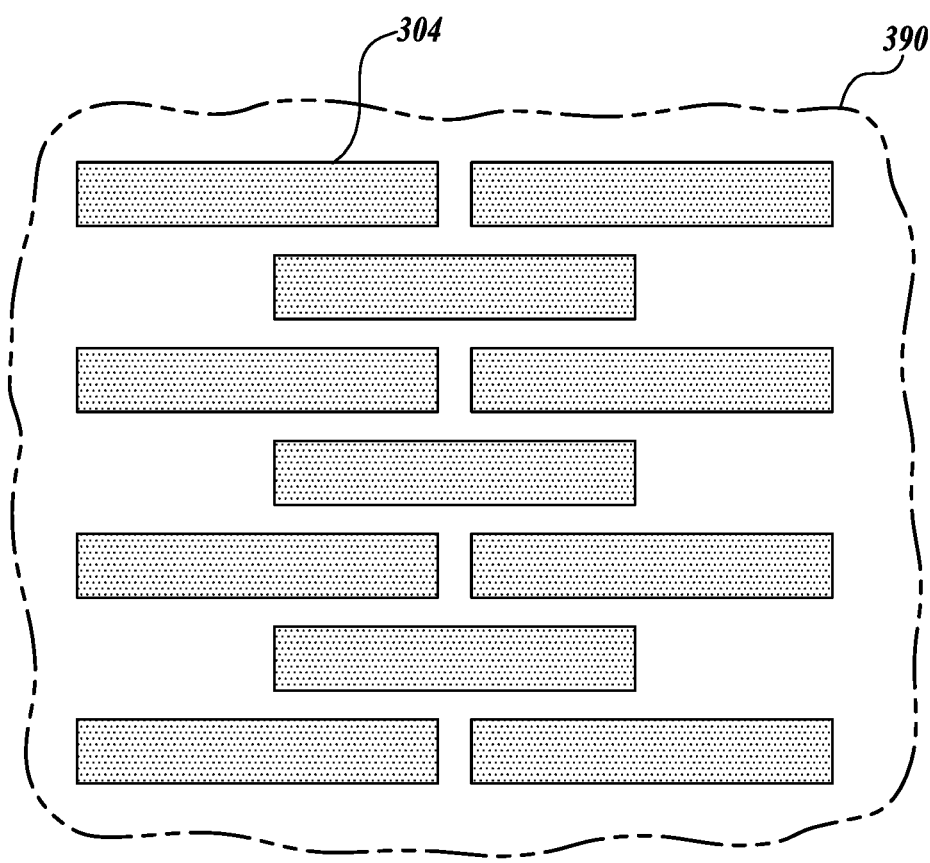
FIG. 3B is a diagrammatical illustration of a discontinuous film.

FIG. 3B is a diagrammatical illustration of a discontinuous film composition having similar discrete micron sized film sections 304 spaced apart and not touching each other that cover an area on the skin surface 390 made using either a stencil or stamp. The film sections 304 are a polygon shape, specifically, rectangles.

Figure 3C:
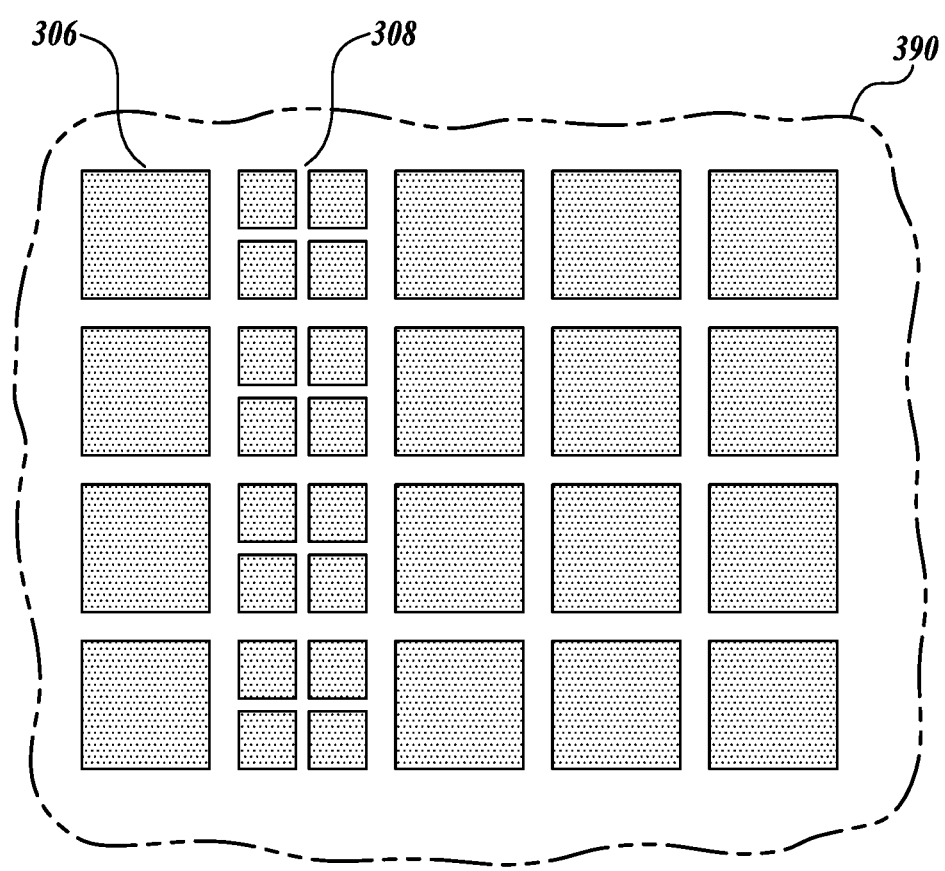
FIG. 3C is a diagrammatical illustration of a discontinuous film.

FIG. 3C is a diagrammatical illustration of a discontinuous film composition having discrete micron sized film sections 306 and 308 spaced apart and not touching each other that cover an area on the skin surface 390 made using either a stencil or stamp. The film sections 306 and 308 are a polygon shape, specifically, squares. The film composition of FIG. 3C shows that film compositions are not limited to being formed from a single shape of film sections, but, can have a plurality of shapes and sizes.

Figure 3D:
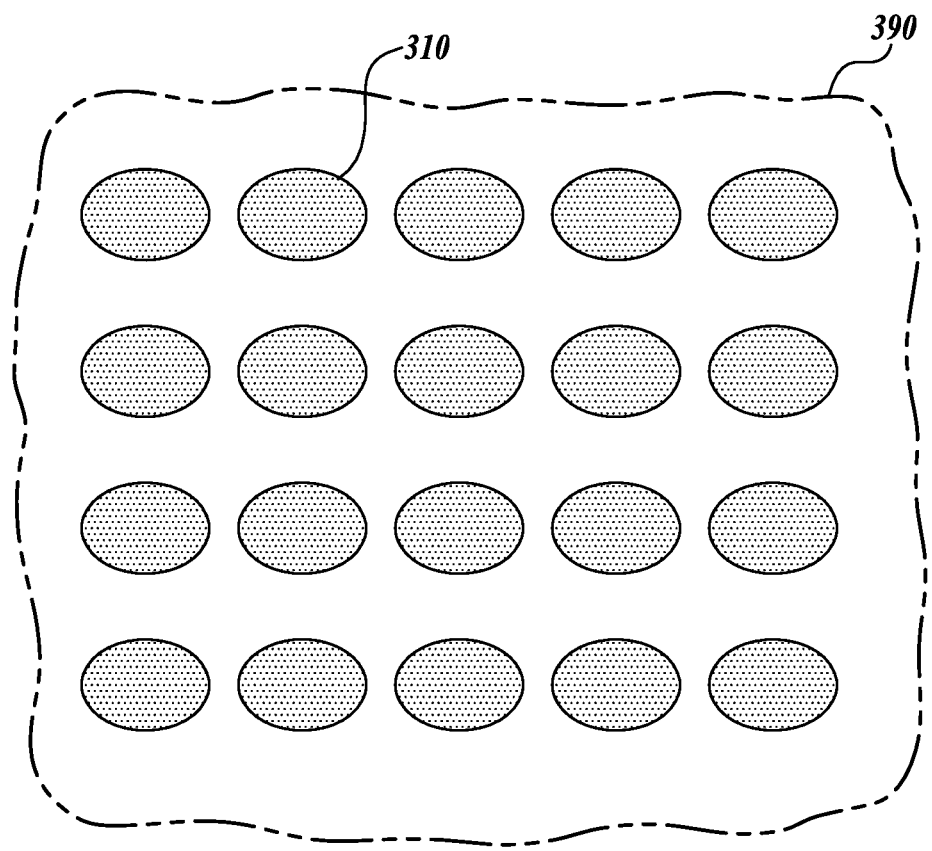
FIG. 3D is a diagrammatical illustration of a discontinuous film.

FIG. 3D is a diagrammatical illustration of a discontinuous film composition having similar discrete micron sized film sections 310 spaced apart and not touching each other that cover an area on the skin surface 390 made using either a stencil or stamp. The film sections 310 are ellipses, other than circles.

Figure 4:
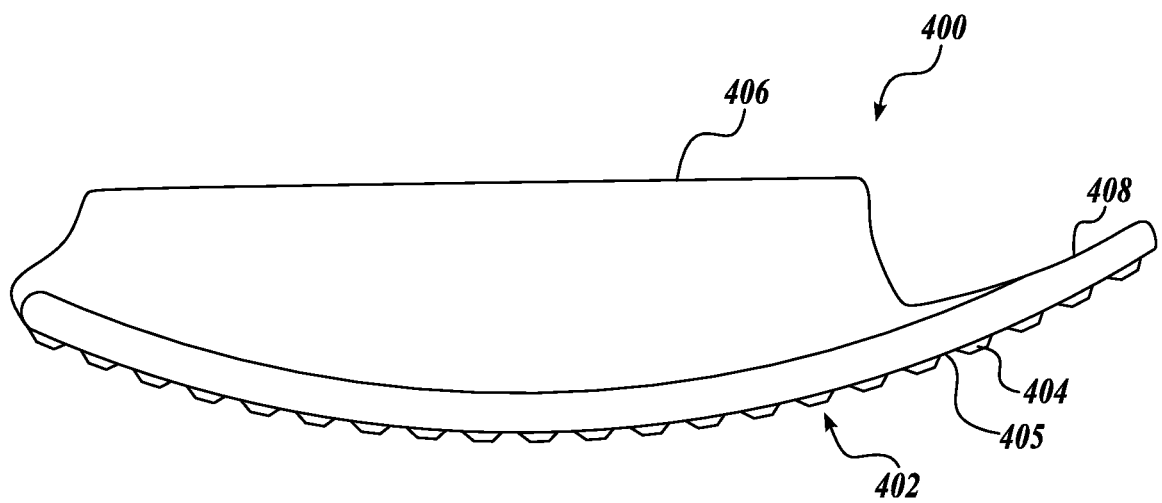
FIG. 4 is a diagrammatical illustration of a stamp.

FIG. 4 is a diagrammatical illustration of an embodiment of a stamp 400 for applying film compositions in a discontinuous manner to skin. In an embodiment, the stamp 400 has an application surface having a plurality of first discontinuous subsurfaces as protrusions 404 separated by a continuous second subsurface of grooves 405, where the plurality of discontinuous subsurfaces are arranged in a repeating pattern.

In an embodiment, the stamp 400 is made from a monolithic material, such as rubber or an elastomer, and is flexible. In an embodiment, the stamp 400 is made from a molding process. The stamp 400 includes a handle 406. The stamping side 402 of the stamp 400 is formed from a membrane 408, being a thin pliable layer. The membrane 408 portion in addition to having a thickness (as shown) also extends in both the length and width (in and out of page) dimensions. In an embodiment, the membrane 408 is convex in all directions, meaning that the membrane 408 curves upward from the center toward the periphery in all directions which has the center as the lowermost point. In an embodiment, the outline of the membrane 408 in the length and width dimension appears as a "comma" shape or a kidney shape with a large and small lobe on opposite ends. The membrane 408 has formed thereon a plurality of protrusions 404 projecting normal from the side 402 of the membrane 408. The protrusions 404 are arranged on the side 402 in both the length and width dimensions. A majority of the outward facing surfaces on the distal end of the protrusions 404 have a similar shape.

Figure 5:
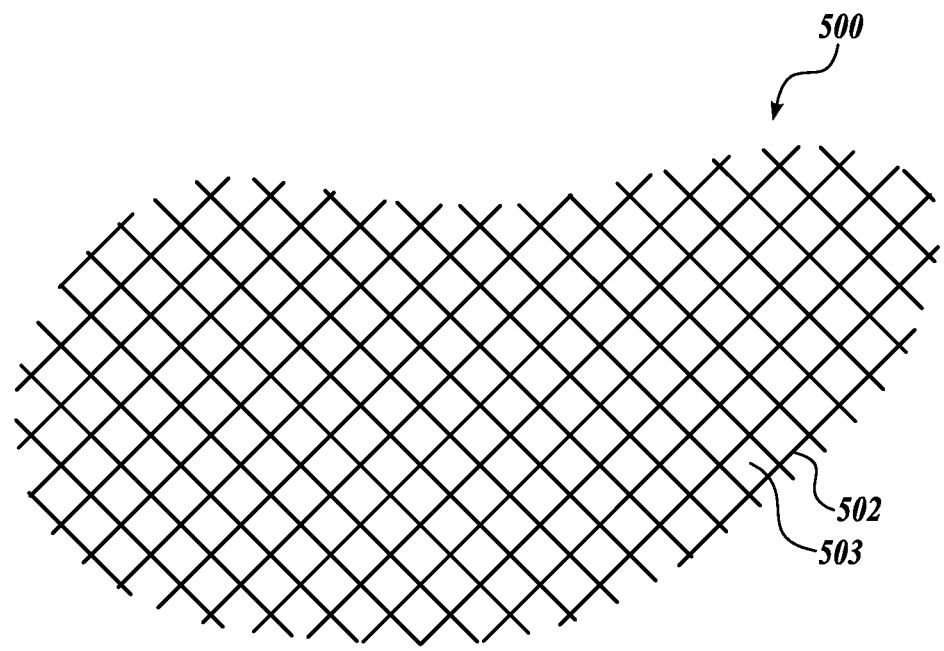
FIG. 5 is a diagrammatical illustration of a stencil.

FIG. 5 is diagrammatical illustration of an embodiment of a stencil 500. In an embodiment, the stencil 500 has an application surface having a plurality of first discontinuous subsurfaces as open holes 503 separated by a continuous second subsurface of ribs or strips 502, where the plurality of discontinuous subsurfaces are arranged in a repeating pattern.

The stencil 500 is formed from a criss-cross pattern of plastic filaments 502. The consequence of criss-crossing plastic filaments is the creation of a plurality open spaces. The stencil 500 of FIG. 5 includes a first and second major surface forming opposite sides, wherein the first and second surfaces are separated by the thickness of the plastic filaments. In an embodiment, the majority of the open spaces of the stencil 500 are similar. In an embodiment, in its undisturbed state, the stencil 500 is planar but upon use on a skin surface, the stencil 500 flexes to accommodate curves on the skin surface. In an embodiment, the outline of the stencil 500 in the length and width dimension appears as a "comma" shape or a kidney shape with a large and small lobe on opposite ends. In an embodiment, the membrane 408 of FIG. 4 has a similar outline as the stencil of FIG. 5.

Figure 6:
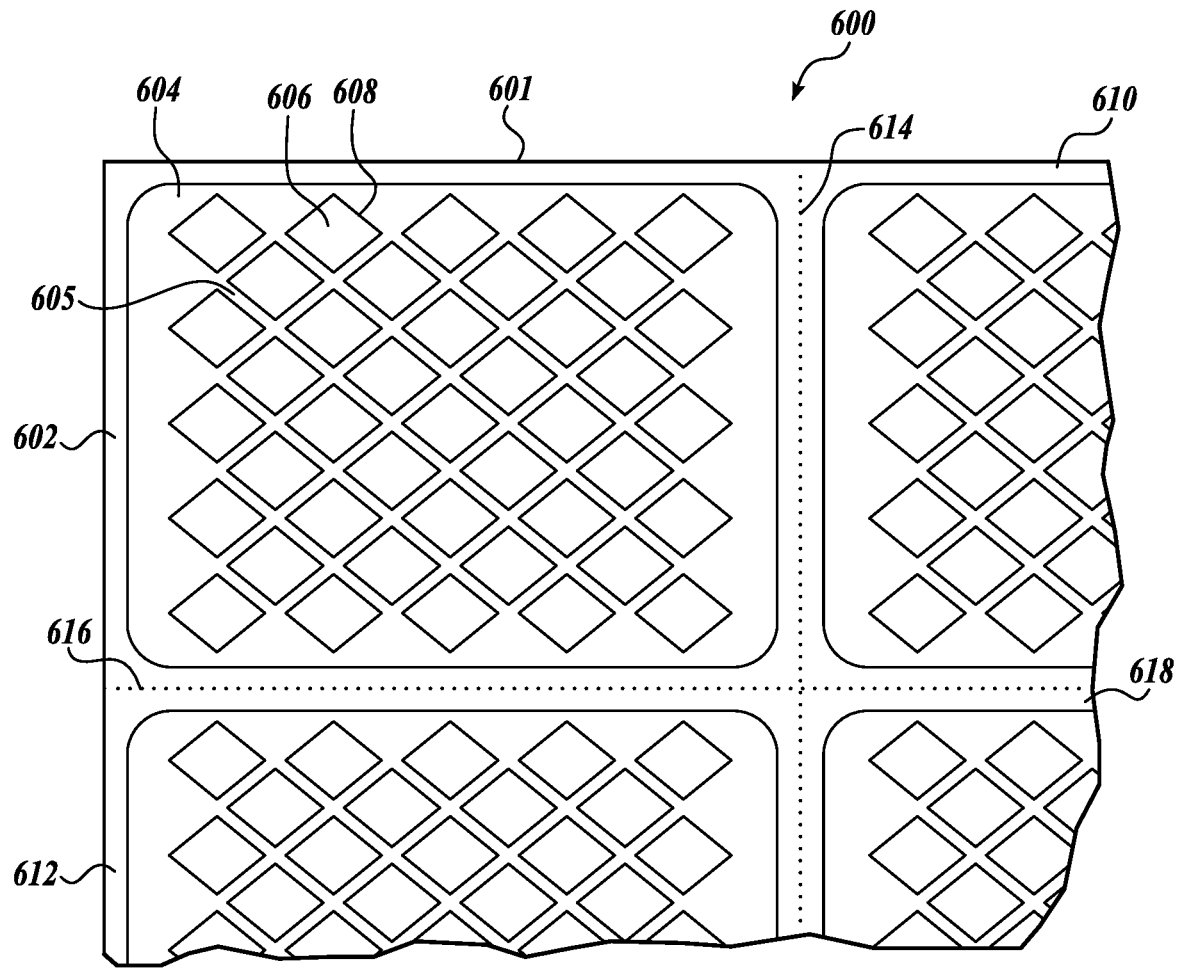
FIG. 6 is a diagrammatical illustration of a stencil.

FIG. 6 is a diagrammatical illustration of an embodiment of a plurality 600 of stencils provided on a larger substrate or backing sheet. In an embodiment, a stencil 604 has an application surface having a plurality of first discontinuous subsurfaces as open holes 606 separated by a continuous second subsurface of ribs or strips 605, where the plurality of discontinuous subsurfaces are arranged in a repeating pattern.

Shown are four stencil sections 602, 610, 612, and 618. The four stencil sections 602, 610, 612, and 618 are connected through a common backing sheet 601. The backing sheet is perforated along lines 614 and 616 to easily separate each stencil section 602, 610, 612, and 618 from one another by manually tearing allowed by the perforation. Referring to the upper left stencil section 602 as representative of the others, the stencil section 602 includes the stencil 604 adhered to the backing sheet 601 via an adhesive. The stencil 604 is entirely included within the boundaries delineated by the perforated lines 614 and 616. The stencil 604 is cut into a pattern including similar open hole shapes 606 by cutting along lines 608, leaving strips 605 of material. Cutting along lines 608 will cut through the stencil 604 sheet material, but the cuts 608 are not so deep as to cut the backing sheet 601. The backing sheet 601 is coated with a waxy surface that allows peeling the stencil 604 off the backing sheet and leaving the cut patterns 606 adhered to the backing sheet. The result is a stencil 604 having an adhesive on one major side with a plurality of open spaces.

Figure 7:
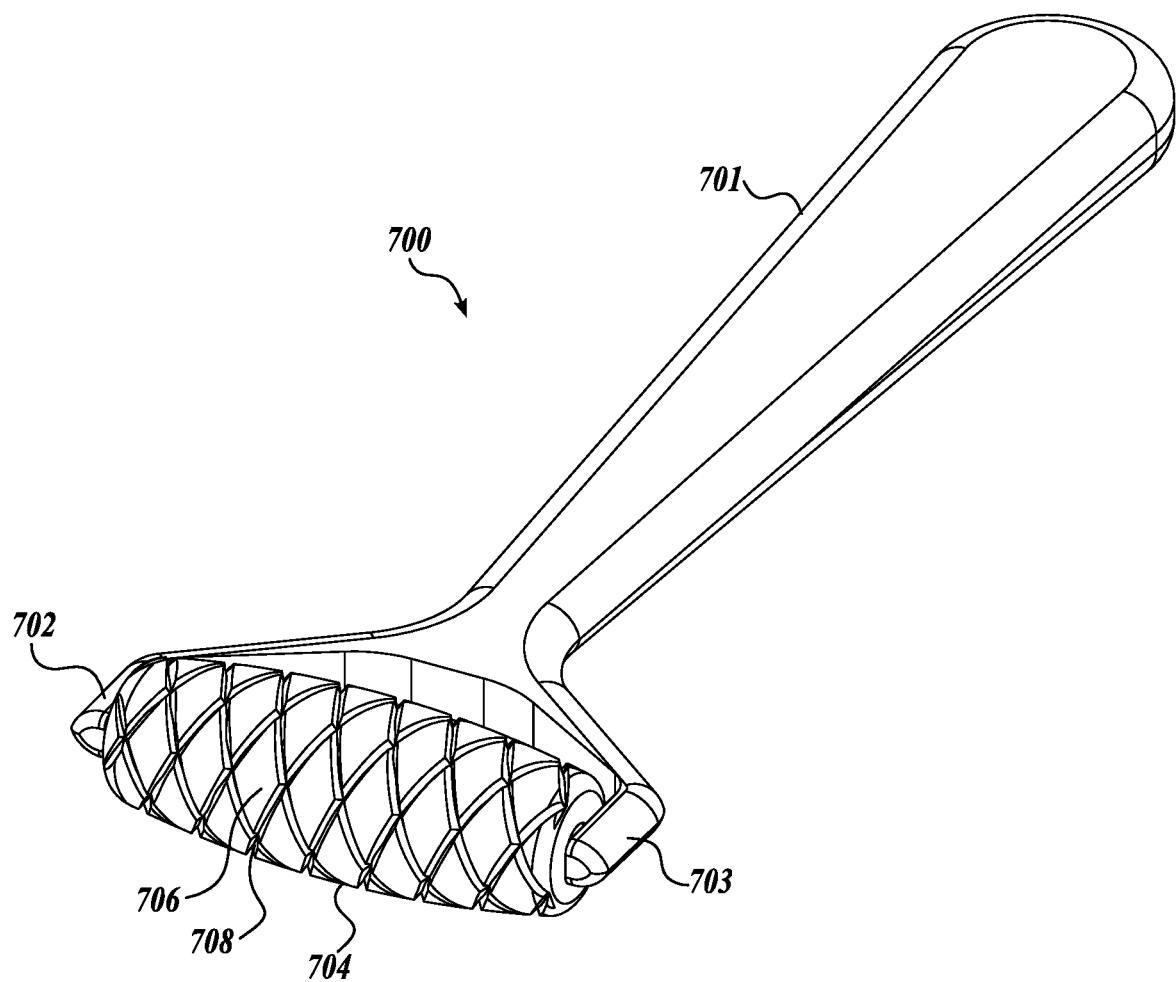
FIG. 7 is a diagrammatical illustration of a rolling stamp applicator.

FIG. 7 illustrates an embodiment of a stamping applicator 700. In an embodiment, the stamp 704 has an application surface having a plurality of first discontinuous subsurfaces as protrusions 706 separated by a continuous second subsurface of grooves 708, where the plurality of discontinuous subsurfaces are arranged in a repeating pattern.

Stamping applicator 700 includes a handle 701 connected to a roller stamp 704 on both ends thereof via the use of two arms 702 and 703. Roller stamp 704 has a generally cylindrical shape, but with a decreasing diameter from the center of the roller stamp 704 toward the ends. In an embodiment, the roller stamp 704 can have a constant diameter. Roller stamp 704 is allowed to roll over surfaces. In an embodiment, roller stamp 704 can include a hollow center and the arms 702 and 703 only partly engage the hollow center by the used of two nubs or pins inserted only partly on either side of the roller stamp 704. This would allow replacing the roller stamp 704 by spreading the arms 702 and 703 apart, and withdrawing the roller stamp 704. In another embodiment, the ends of the roller stamp 704 can be provided with the nubs or pins which are inserted into corresponding hubs on either arm 702, 703. The design of the roller stamp 704 allows for rolling over areas on the skin on which a skin composition is desired to be applied.

In an embodiment, roller stamp 704 is made from an absorbent material, such as foam. A foam can absorb a composition and replenish the outer surface of the roller. Also, the deep cut lines on the roller stamp 704 store composition for replenishing the outer surface. In another embodiment, roller stamp 704 is made from a hard plastic. In an embodiment, the roller stamp 704 is made from a metal. A metal roller stamp 704 has an advantage in that the metal can be actively heated.

As with other stamp applicators disclosed herein, roller stamp 704 includes a geometric pattern in order to produce a discontinuous film on the skin surface. In the FIG. 7, the roller stamp 704 includes diamond shapes 706 placed over the entire circumference from end to end of the roller stamp 704. Individual diamond shapes 706 are produced, for example, by cutting deep notched continuous lines 708 in a criss-cross pattern into the roller stamp 704 material leaving behind the raised surfaces as the diamond shapes 706. However, other embodiments of the roller stamp 704 can include any other shapes as disclosed herein for stamp applicators.

FIGS. 8, 9, 10, and 11 show further embodiments of a stamp applicator. The stamp applicators 710, 810 and 910 will be described hereinafter simultaneously, the elements common to the three embodiments being designated by the same reference numerals.

Figure 10:
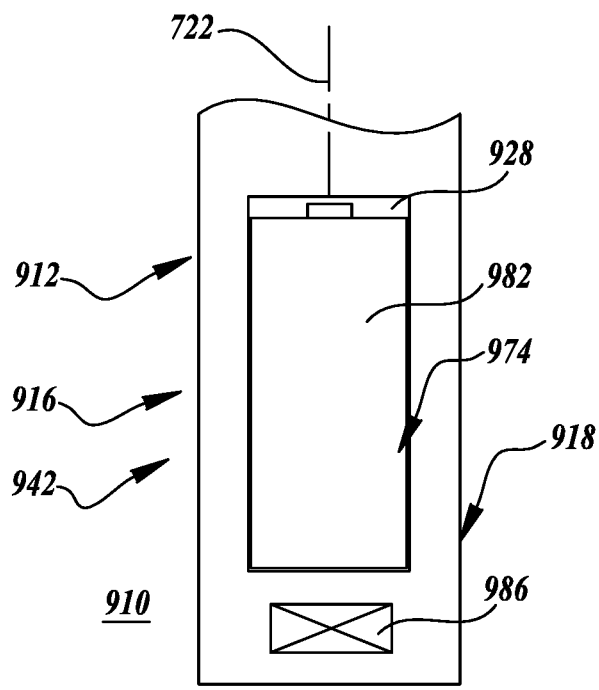
FIG. 10 is a diagrammatical illustration of a cross section of a rolling stamp applicator.

The stamp applicator 710, 810, 910 comprises: a handle 712, 812, 912; a stamp roller 714; and a applicator 716, 816, 916 for electrically heating the stamp roller 714. The roller 714 of the stamp applicator 910 is not shown in FIG. 10. The handle 712, 812, 912 has a main portion 718, 818, 918 and two arms 720. In FIG. 10, the arms 20 of the handle 912 are not shown and the main portion 918 is partially shown. The main portion 718, 818, 918 extends substantially along a first axis 722. A first end of said main portion is extended by said two arms 720, which deviate from each other along the first axis 722 and then curve towards each other, in a plane comprising said first axis. Each arm 720 has a free end 724, the two free ends 724 being located at a distance from one another on a second axis 726. The second axis 726 is substantially perpendicular to the first axis 722. The handle 712, 812, 912 comprises an internal cavity 728, 828, 928, which extends inside the main part 718, 818, 918 and each of the two arms 720. The gripping handle 712, 812, 912 is made of an elastically deformable material, at least at the level of the arms 720. In particular, said arms 720 are flexible so as to allow the two free ends 724 to be separated and brought closer together. One compared to the other. The handle 712, 812, 912 is made of thermoplastic polymer. Alternatively, the handle is made of metal or wood.

Figure 11:
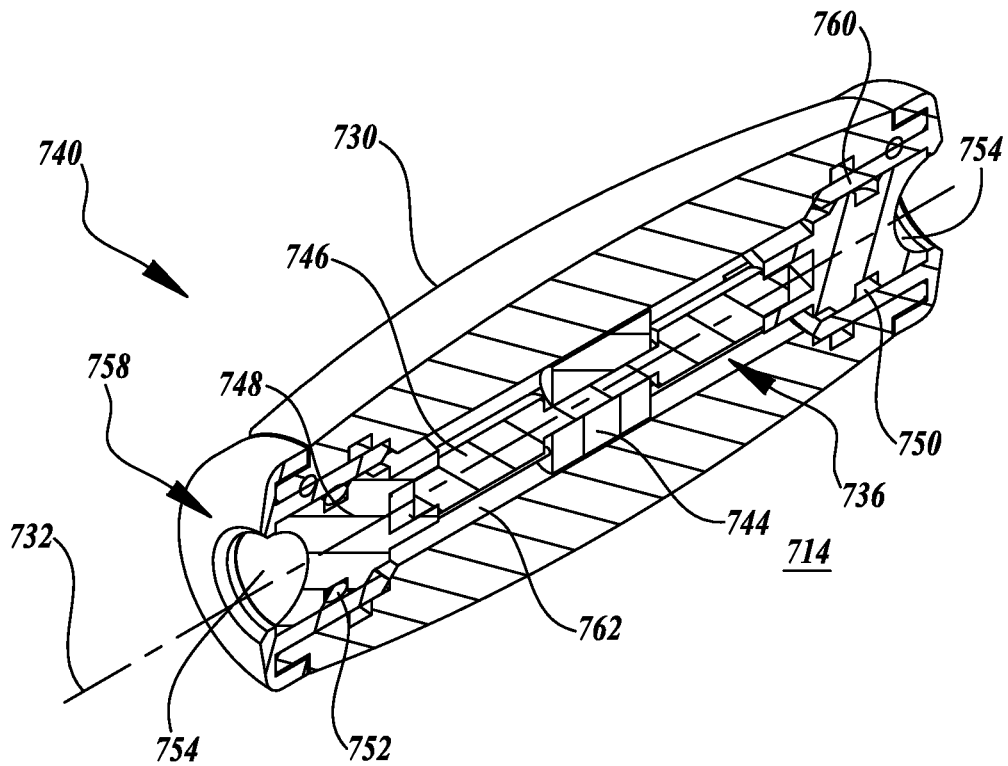
FIG. 11 is a diagrammatical illustration of a cross section of the rolling stamp applicator of FIG. 7.

The stamp roller 714 of the stamp applicator 710, 810, 910 is shown in longitudinal section in FIG. 11. The stamp roller 714 has an outer surface 730 of substantially circular shape about a third axis 732.

The stamp roller 714 further comprises a through internal cavity 736, extending along the third axis 732. The stamp roller 714 is made of a good thermal conductive material and/or having a good thermal inertia, for example of stone or metal type.

Figure 8:
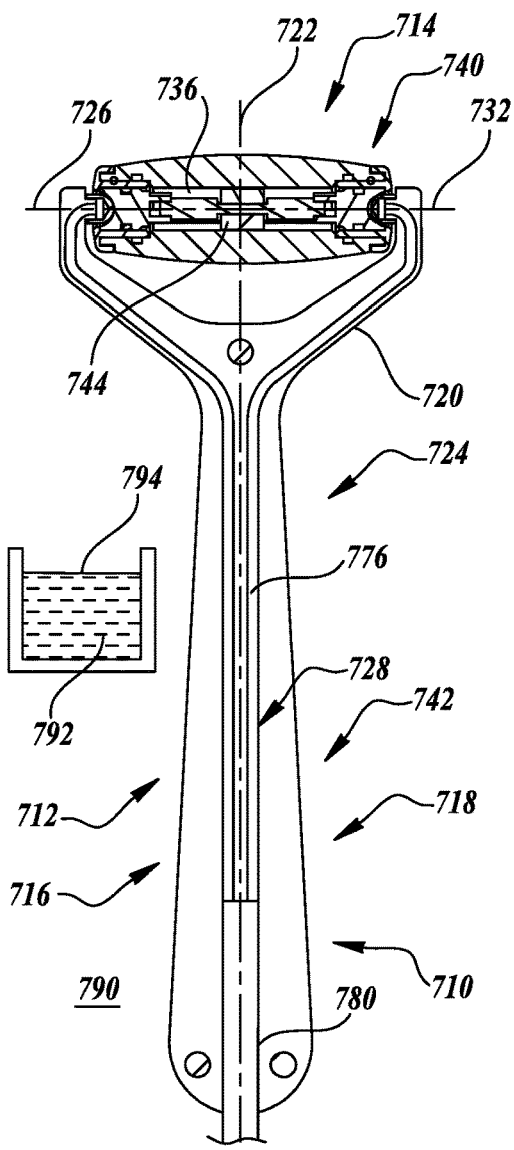
FIG. 8 is a diagrammatical illustration of a cross section of the rolling stamp applicator of FIG. 7.
Figure 9:
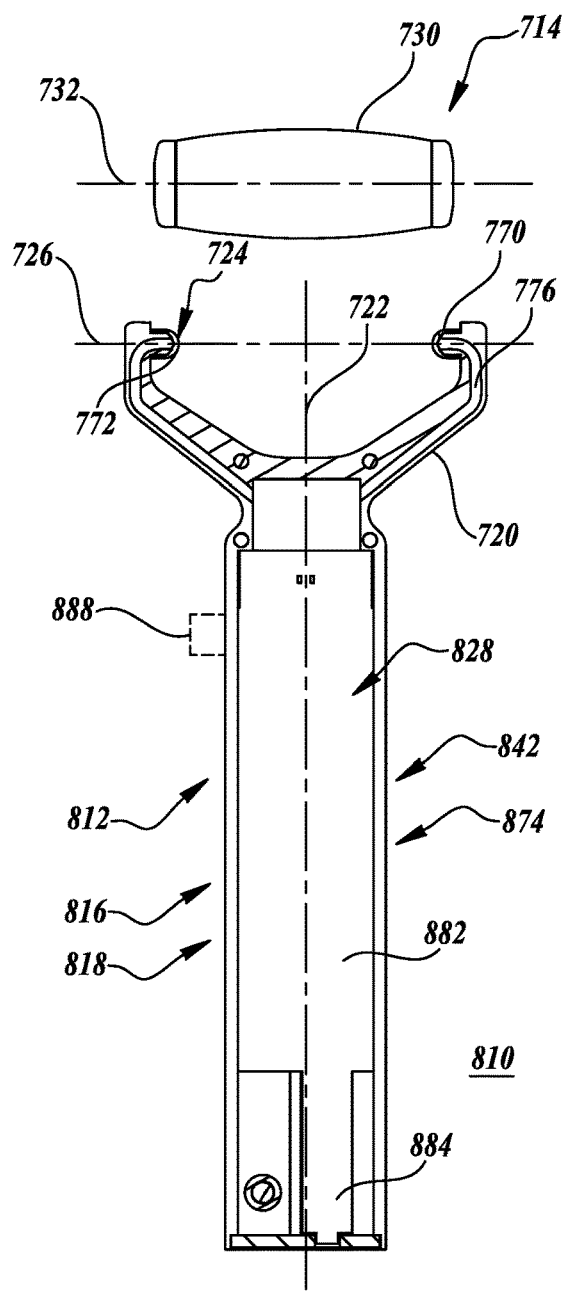
FIG. 9 is a diagrammatical illustration of a rolling stamp applicator.

The stamp roller 714 is adapted to be removably connected to the handle 712, 812, 912. In an assembled configuration, as shown in FIG. 8 for the stamp applicator 710, the second 726 and third 732 axes are confused. FIG. 9 shows the stamp applicator 810 with the handle 812 and the stamp roller 714 in a dissociated configuration.

The heating applicator 716, 816, 916 comprises a first part 740, integral with the roller 714, and a second part 742, 842, 942, integral with the handle 712, 812, 912.

The first part 740, visible in FIGS. 8 and 11, is housed in the internal through cavity 736 of the roll 714. The first part 740 of the heating device 716, 816, 916 comprises at least one electric heating element 744, for example an electrical resistance. In the embodiment of FIGS. 8 and 11, the first part 40 comprises two electrical resistors 744 arranged facing the third axis 732. The first part 740 further comprises an electrically insulating rod 746, extending along the third axis 732 and serving as a support for the electrical resistors 744.

The first portion 740 further comprises two electrically conductive pads 748. Each stud 748 is fixed to one end of the insulating rod 746 and electrically connected to one end of each of the electrical resistors 744. A lateral surface of each stud 748 has a groove 750 receiving a gold seal 752. Opposite the insulating rod 746, each stud 748 comprises a first assembly element 754. Said first assembly element 754 is intended for the mechanical connection of the roll 714 with the handle 712, 812, 912, as well as at the electrical connection of the first portion 740 and the second portion 742, 842, 942 of the heater 716, 816, 916.

In the embodiment of FIGS. 8 and 11, each first assembly member 754 has substantially the shape of a concave surface. Said concave surface notably has a shape of revolution around the third axis 732. The first two assembly elements 754 are substantially identical. Each stud 748 and each first assembly element 754 is formed of an electrically conductive material such as a metal.

In the embodiment of FIGS. 8 and 11, the first portion 740 of the heating device further comprises two covers 758 electrically insulating. Each cap 758 is inserted at one end of the internal through-cavity 736 of the roller 714. Each cap 758 comprises in particular a cylindrical portion 760 disposed around a stud 748, at the level of the groove 750. The covers 758 and the O-rings 752 provide a watertightness of the inner through cavity 736 and the electrical resistors 744. The first portion 740 further comprises an additional O-ring disposed between each pad 748 and each corresponding cylindrical portion 760.

The cylindrical portion 760 further provides electrical insulation between the pad 748 and the roller 714, especially in the case where the latter is made of metal. The first portion 740 of the heating device further comprises a fluid 762 of fat type, thermally conductive and electrically insulating. The fluid 762 fills the inner through-cavity 736 of the roller 714 around the electrical resistances 744 and the insulating rod 746. The thermally conductive fluid 762 optimizes the heat transfer between the resistors 744 and the roller 714. The second portion 742, 842, 942 of the heater 716, 816, 916 includes two second connecting members 770, each of said second connecting members being disposed at the free end 724 of one of the arms 720 of the handle 712, 812, 912. Each of the second connecting members 770 is intended to cooperate with a first connecting element 754 for the mechanical connection of the roller 714 with the handle 712, 812, 912 and for the electrical connection of the first portion 740 and the second portion 742, 842, 942 of the heater 716, 816, 916.

Each second assembly element 770 has the shape of a pin comprising an outer surface 772, convex and of revolution. The outer surface 772 is able to fit into the concave surface of a first connecting element 754. The outer surface 772 and the concave surface of the first connecting element 754 have a partial contact, so that minimize rotational friction.

The outer surfaces 772 of the two second joining members 770 are substantially identical. The roller 714 can thus be assembled in both directions with the handle 712, 812, 912.

The second portion 742, 842, 942 of the heating device further comprises a member 774, 874, 974 for supplying the heating element 44 with power. The supply member 774, 874, 974 comprises in particular two conductive wires 776, extending into the internal cavity 728, 828, 928 of the handle, at the arms 20. A first end of each of the conductive wires 776 is connected to one of the second connecting elements 770.

In the embodiment of FIG. 11, the heating device 716 further comprises an electric cable 780 connected to a second end of the conductive wires 776. The electrical cable 780 extends outside the main portion 718 of the handle gripper 712 from a second end of said main portion, opposite to the arms 720. The electric cable is equipped with means (not shown) for connection to a low voltage electrical power source, USB type.

In the embodiments of FIGS. 9 and 10, the feed member 874, 974 comprises an electric generator 882, 982 disposed in the internal cavity 828, 928 of the handle, at the main portion 818, 918.

In the embodiment of FIG. 9, the electric generator 882 is a battery-type electric accumulator and the power supply member 874 further comprises a device 884 for connecting said electric accumulator to a source of electrical energy. The device 884 is for example a USB port.

According to a variant not shown, the electrical generator 882 is of nonrechargeable battery type, which improves the liquid tightness of the handle 812, eliminating the openings giving access to the internal cavity 828.

In the embodiment of FIG. 10, the electric generator 982 is an induction rechargeable battery type electric accumulator. The supply member 874 further comprises an induction coil 986 disposed at a second end of the main portion 918 of the handle, opposite the arms 720. The induction coil 986 is adapted to cooperate with an external charger (not shown) for recharging the electric accumulator 982. Such an induction charging system is known in particular for devices of the electric toothbrush type, as described for example in the document WO2015147054. This embodiment allows non-contact reloading and good liquid sealing of the sleeve 912. The power supply member 774, 874, 974 further comprises an electronic module (not shown) for regulating the power supply of the resistors 744.

This electronic module comprises, for example, a system for regulating the heating temperature. and/or a timer system. As an indication, a temperature of the outer surface 730 of the roll is limited to 50° C. by the electronic module. The power supply element 774, 874, 974 further comprises a switch 888 (FIG. 2) enabling the power supply of the resistors 744 to be turned on and off.

The stamp applicator 710, 810, 910 is part of an assembly 790 for the cutaneous application of a fluid cosmetic composition 792 (FIG. 8).

In an embodiment, a cosmetic composition has a viscosity which decreases when its temperature increases. This is for example a wax-like facial mask composition.

A method of mounting the stamp applicator 710, 810, 910 will now be described. It is considered that said stamp applicator is in the dissociated configuration of FIG. 9. In order to assemble the handle 712, 812, 912 and the stamp roller 714, a user assembles one of the second assembly members 770 said handle with one of the first assembly elements 754 of said roller. The user then exerts a mechanical force on the arms 720 of the handle in order to move them away from one another, in order to assemble the other second assembly element 770 with the other first assembly element 754. the force on the arms 720 is then released and the stamp applicator 710, 810, 910 is in the assembled configuration of FIG. 1.

In said assembled configuration, the complementary internal 756 and outer surfaces 772 of the connecting elements 754, 770 form a pivot connection between the handle 712, 812, 912 and the roller 714, around the second axis 726. A distance between the second connecting elements 770 along the second axis 726 is slightly greater in the assembled configuration than in the dissociated configuration. Thus, in assembled configuration, the arms 720 exert a slight elastic compression on the roller 714, which improves the electrical contact between the inner 756 and outer surfaces 772. Said electrical contact makes it possible to form a closed electrical circuit between the first part 740 and the second part 742, 842, 942 of the heating device 716, 816, 916, in particular by actuating the switch 888.

A method of using the stamp applicator 710, 810, 910 will now be described. The switch 888 is operated to supply power to the resistors 744. The temperature of the outer surface 730 of the roll increases. The roll 714 is then rolled against a surface 794 of the cosmetic composition 792. Said composition softens on contact with the hot roll; the outer surface 730 is thus loaded in a fluid cosmetic composition. The roller 714 is then applied to the skin of a user, for example on the face. The stamp applicator 710, 810, 910 is moved so as to deposit cosmetic composition 792 on the skin of the user, by rolling the roller. The contact of the hot outer surface with the skin also provides a massaging effect.

The cosmetic composition 792 then cools forming a film on the skin. As a variant, the cosmetic composition 792 penetrates into the epidermis, the penetration being improved by the heat of the roller 714. As an alternative to the method of use described above, the cosmetic composition 792 is deposited manually on the skin, and then the hot roller 714 is applied. The hot stamp applicator 710, 810, 910 can also be used without a cosmetic composition, to stamp the face or another part of the body.

To clean the stamp applicator 710, 810, 910, the handle 712, 812, 912 and the stamp roller 714 are dissociated by a method that is the reverse of the above described method of assembly. If necessary, the tightness of the handle and the roller allows their cleaning with water without risk of short circuit.

The Compositions

In an embodiment, any stencil or stamp disclosed herein is provided in combination with a film forming composition, particularly skin-tightening compositions, as a combination package. For example, a consumer wishing to purchase a skin-tightening composition receives a stencil or a stamp for applying the composition together with the composition in the same package. This allows the matching of a particular film composition with the stencil or stamp that works most effectively with the composition.

In one embodiment, the disclosure relates to compositions for tightening the skin, said compositions comprising at least one thermoplastic elastomer, at least one adhesive polymer, and at least one filler, wherein the at least one thermoplastic elastomer has at least two glass transition temperatures ($T_g$).

In an embodiment, the compositions may be effective at reducing the appearance of skin imperfections. In various embodiments, the compositions may improve the appearance of the skin by forming a film on the skin that has a Young Modulus greater than that of skin, and thus has the capability of tightening the skin.

As used herein, the term "tighten" means that the film contracts in a manner that skin has a tighter feel to the user, and that reduces the visual appearance of wrinkles in the skin.

In further embodiments, the disclosure relates to a skin-tightening film comprising at least one thermoplastic elastomer, at least one adhesive polymer, and at least one filler, wherein the at least one thermoplastic elastomer has at least two glass transition temperatures (Tg), wherein the film has a Young Modulus greater than about 500 kPa.

Film forming polymers for application on the skin are disclosed in U.S. Pat. No. 8,771,656, incorporated herein expressly by reference. In an embodiment, a film includes anionic copolymers based on methacrylic acid and methyl methacrylate in a random, block, or alternating configuration. In U.S. Pat. No. 9,050,474, incorporated herein expressly by reference, a class of polymers known as organopolysiloxanes is disclosed as film forming polymers for application on the skin. In an embodiment, organosiloxanes include polydimethylsiloxane (PDMS or Dimethicone). Additionally, in an embodiment, silicone polymers are copolymerized with other polymers, such as polyurethanes and ethylenically unsaturated monomers or polymers thereof. U.S. Pat. No. 8,277,791, incorporated herein expressly by reference, discloses film forming polymers include silicone polyurethane polymers in combination with at least one elastomer selected from silicone gums, polyisobutylene, natural rubbers, and block-copolymer rubbers.

In an embodiment, the film composition is a skin-tightening composition. In an embodiment, skin-tightening film compositions are disclosed in WO 2016/100742 and WO 2016/100690, both incorporated herein expressly by reference. In an embodiment, a skin-tightening film composition includes an elastomer, an adhesive film forming polymer, and a filler. In an embodiment, a skin-tightening composition includes at least one thermoplastic elastomer chosen from amorphous hydrocarbon block copolymers of styrene and monomers of hydrocarbon containing 2 to 5 carbon atoms and comprising one or two ethylenic unsaturations, and having a first $T_g$ below about 0° C., and a second $T_g$ greater than about 25° C.; at least one adhesive film-forming polymer chosen from polymer particles of $C_1$-$C_4$ alkyl (methacrylate)polymer, stabilized in a nonaqueous dispersion; and at least one filler. In an embodiment, the thermoplastic elastomer includes one or more styrene blocks and one or more blocks of units selected from butadiene, ethylene, propylene, butylene, isoprene, or mixtures thereof. In an embodiment, the thermoplastic elastomer is a diblock copolymer chosen from styrene-ethylene/propylene copolymers, styrene-ethylene/butadiene copolymers, styrene-ethylene/butylene copolymers, styrene-butadiene, or styrene-isoprene copolymers; a triblock copolymer chosen from styrene-ethylene/propylene-styrene copolymers, styrene-ethylene/butadiene-styrene copolymers, copolymers of styrene-isoprene-styrene, or copolymers of styrene-butadiene-styrene; or mixtures thereof. In an embodiment, adhesive polymers include $C_1$-$C_4$ alkyl (meth)acrylate and ethylenically unsaturated acid monomer of $C_1$-$C_4$ alkyl(methacrylate) polymer in an oil dispersion. In an embodiment, the $C_1$-$C_4$ alkyl(methacrylate)polymer is chosen from methyl (meth)acrylate, ethyl (meth)acrylate, n-propyl (meth)acrylate, isopropyl (meth)acrylate, n-butyl (meth)acrylate and tert-butyl (meth)acrylate polymers. In an embodiment, the oil is a hydrocarbon based oil of up to 40 carbon atoms, such as isododecane. In an embodiment, the filler is chosen from silica particles, hydrophobic silica aerogel particles, or aerogel particles of hydrophobic silica surface-modified with trimethylsilyl groups. In an embodiment, film-forming compositions include volatile organic solvents, volatile hydrocarbon-based oils, or volatile silicone oils. In an embodiment, the solvent is chosen from branched $C_8$ to $C_{16}$ alkanes, $C_8$ to $C_{16}$ isoalkanes, isododecane, isodecane, isohexadecane, octamethyltetrasiloxane, decamethylcyclo-pentasiloxane, dodecamethylcyclohexasiloxane, heptamethyloctyltrisiloxane, hexamethyldisiloxane, decamethyltetrasiloxane, dodecamethylpentasiloxane, and mixtures thereof. In an embodiment, silicone elastomers are chosen from silicone crosspolymers, such as dimethicone crosspolymers, dispersed in at least one oil.

In an embodiment, a film composition is disclosed in U.S. application Ser. Nos. 15/087,115 and 15/094,259, entitled, "Systems and Methods for Improving the Appearance of the Skin" and "Compositions for Removing Cosmetic Films," both are incorporated herein expressly by reference. In an embodiment, a film composition includes one or more thermoplastic elastomers chosen from amorphous hydrocarbon block copolymers of styrene and monomers of hydrocarbon containing 2 to 5 carbon atoms and having one or two ethylenic unsaturations, and having a first $T_g$ (glass transition temperature) below about 0° C., and a second $T_g$ greater than about 25° C.; one or more adhesive film-forming polymers chosen from polymer particles of $C_1$-$C_4$ alkyl (methacrylate)polymer, stabilized in a non-aqueous dispersion; and at least one filler; and a cosmetic composition for making up the skin, comprising at least one organic pigment and optionally at least one volatile solvent. In an embodiment, the cosmetic composition for making up the skin includes organic pigments chosen from nitroso, nitro, azo, xanthene, pyrene, quinoline, anthraquinone, triphenylmethane, fluorane, phthalocyanin, metal complex, isoindolinone, isoindoline, quinacridone, perinone, perylene, diketopyrrolopyrrole, indigo, thioindigo, dioxazine, triphenylmethane and quinophthalone compounds.

The film forming compositions explicitly recited are not meant to be exhaustive, but merely are provided to give exemplary films that are pertinent to this disclosure.

In addition to the film forming polymers, the film compositions include any number of additional ingredients depending on the purpose of the film. In an embodiment, the film includes one or more cosmetic ingredients selected from humectants emollients, moisturizers, skin-tightening ingredients, anti-wrinkle ingredients, concealers, matte finishing agents, pigments, colorants, proteins, anti-oxidants, bronzers, chelating agents, emulsifiers, ultraviolet (UV) absorbing agents, oil absorbing agents, anti-foam agents, anti-tack agents, thickeners, fragrances, preservatives, antimicrobials, fungistats, neutralizing agents, vitamins, plasticizers, cohesion agents, basifying and acidifying agents, fillers, solvents, and combinations thereof.

In an embodiment, a film is a film that is adhered to facial features, including around the eyes, lips, cheeks, forehead, neck area. In an embodiment, a film is a film that is adhered on the skin.

In an embodiment, a film is a skin-tightening film. In an embodiment a film is a long wearing film, also known as a long lasting film. In an embodiment, a long wearing or long lasting film is any film that is worn for up to or more than 10 minutes. In an embodiment, a long wearing film is any film that is worn for up to or more than 20 minutes. In an embodiment, a long wearing film is any film that is worn for up to or more than 30 minutes. In an embodiment, a long wearing film is any film that is worn for up to or more than 1 hour. In an embodiment, a long wearing film is any film that is worn for up to or more than 2 hours. In an embodiment, a long wearing film is any film that is worn for up to or more than 4 hours. In an embodiment, a long wearing film is any film that is worn for up to or more than 6 hours. In an embodiment, a long wearing film is any film that is worn for up to or more than 12 hours. In an embodiment, a long wearing film is any film that is worn for up to or more than 24 hours.

In an embodiment, the skin-tightening compositions comprise from 0.1 to 20% by weight of at least one tensioning agent, with respect to the total weight of the composition, and at least one dispersion in a liquid fatty phase of solid particles of a grafted ethylenic polymer, as disclosed in U.S. 2007/0224158.

The tensioning agent can be chosen in particular from: a) synthetic polymers; b) polymers of natural origin; c) mixed silicates; d) wax microparticles; e) colloidal particles of inorganic fillers; and the mixtures of these.

The synthetic polymers which can be used as tensioning agent can be chosen from: polyurethane polymers and copolymers; acrylic polymers and copolymers; polymers of sulphoisophthalic acid; grafted silicone polymers; water-soluble or water-dispersible polymers comprising water-soluble or water-dispersible units and LCST units; non-elastomeric and water-insoluble film-forming linear ethylenic block polymers exhibiting a dynamic storage modulus E' at 1 Hz and at 22° C. of greater than 200 MPa; a dispersion in a liquid fatty phase of solid particles of a grafted ethylenic polymer exhibiting a glass transition temperature of greater than 40° C., and mixtures of these.

Other tensioning agents which can be used comprise microdispersions of wax particles. They are dispersions of particles having a diameter generally of less than 5 μm or better still of less than 0.5 μm and composed essentially of a wax or of a mixture of waxes chosen, for example, from carnauba, candelilla or alfa waxes.

US 2017/0216185 describes a skin-tightening test as follows. The test consists in comparing, in vitro, the tightening power of the polymer to be evaluated, with respect to a reference tightening polymer: Hybridur®875 polymer dispersion from Air Products (40% by weight aqueous dispersion of particles of an interpenetrated network of polyurethane and acrylic polymers). The polymer to be evaluated is deposited on a nitrile rubber strip cut from a glove sold under the reference Safeskin Nitrile Criticial No. 038846 by Dominique Dutscher SA, with a surface area of 3.5 $cm^2$ stretched taut beforehand on a support. An aqueous solution containing the polymer to be evaluated is thus deposited on the elastomer strip, by depositing 1.8 mg (as dry matter) of polymer.

26 μl of an aqueous solution containing 7% AM of Hybridur®875 polymer were thus deposited on a nitrile rubber strip in order to thus obtain a reference tightening strip, and 26 μl of a solution containing the polymer to be evaluated in an isododecane/ethanol mixture (70/30 weight/weight) were deposited on another strip. After drying at room temperature (25.degree. C.) for 24 hours, the curving (retraction) of the strip treated with the polymer is observed in comparison with that obtained with the control (Hybridur®875).

The tightening effect, obtained according to the protocol described above, of polymers can be measured. The resistance to water of the tightening effect can also be evaluated by immersing the rubber strips treated with the polymer to be evaluated in water at ambient temperature (25° C.) for 10 minutes, followed by evaluating the tightening effect after drying for 1 hour.

Combination Kits

Figure 12:
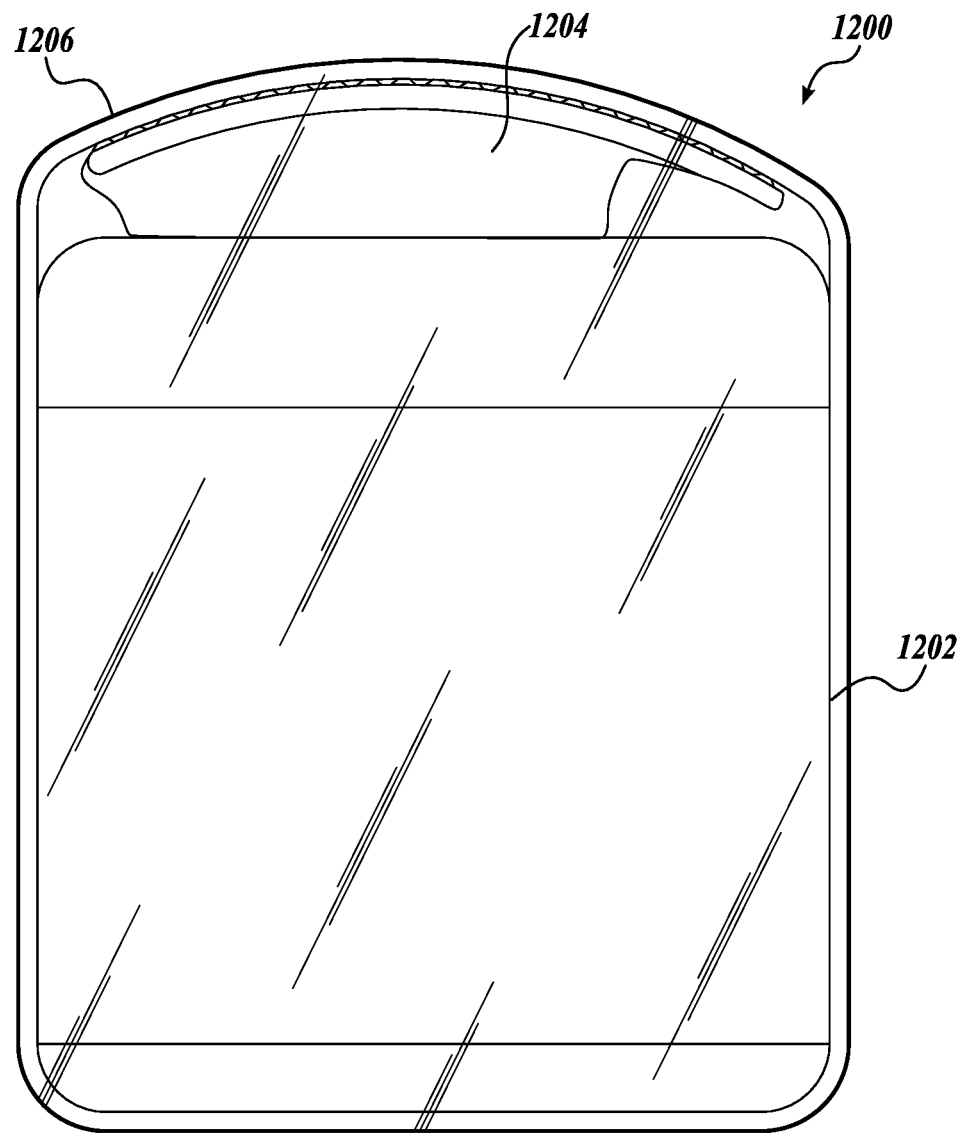
FIG. 12 is a diagrammatical illustration of a combination of a skin-tightening composition in a container and a stamp provided as a kit or unit.

FIG. 12 is a diagrammatical illustration of a combination of a skin-tightening composition in a container 1202 and a stamp 1204 provided as a kit or unit 1200. The container 1202 is any jar, tube, or other container suitable to contain a skin-tightening composition. The stamp 1204 is shown only as an example of an applicator, and is any suitable stamp or stencil disclosed herein. The container 1202 and applicator 1204 are held by shrink-wrap 1206, for example. However, other suitable packaging is used to hold the applicator 1204 to the container 1202.

Figure 13:
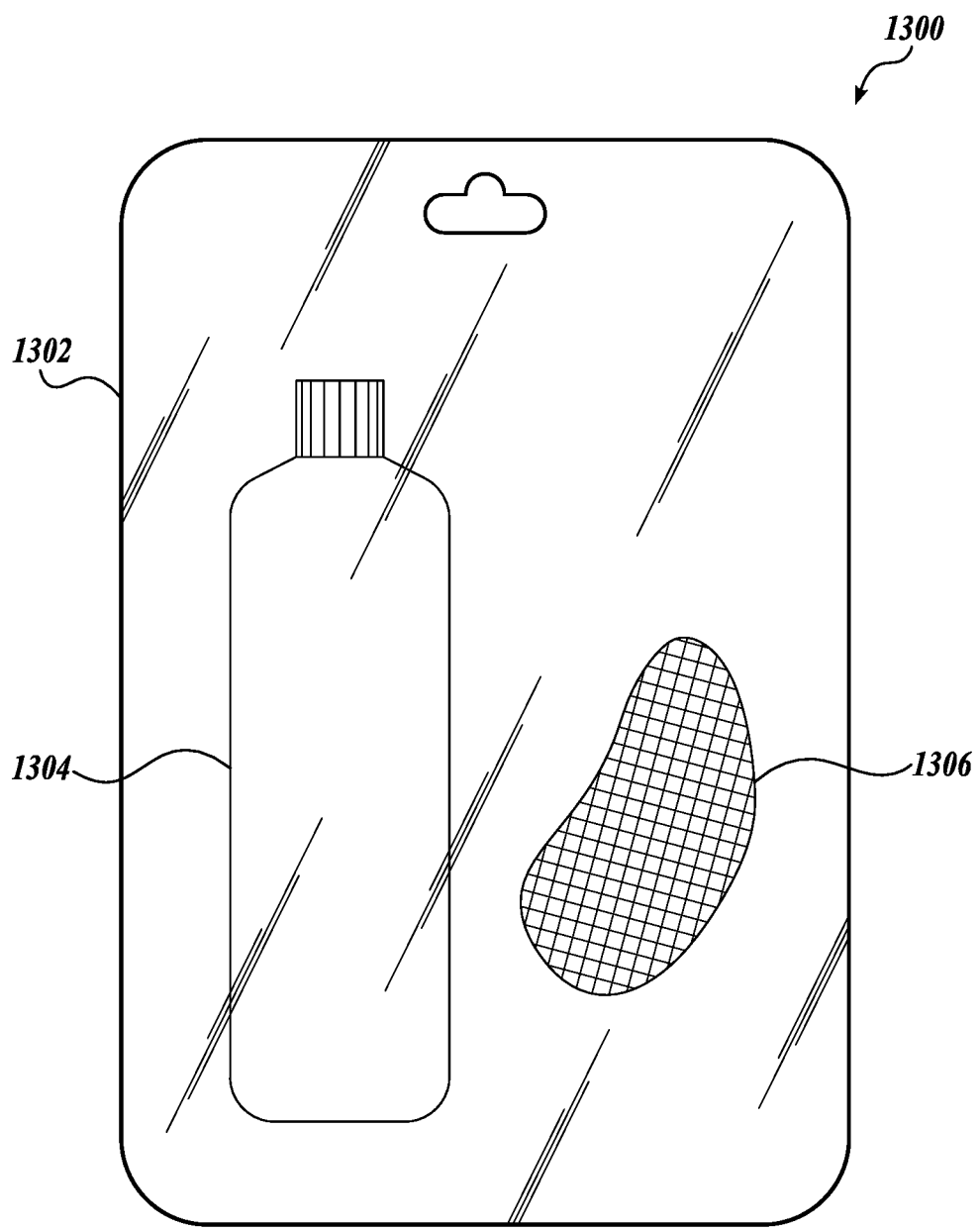
FIG. 13 is a diagrammatical illustration of a combination of a skin-tightening composition in a container and a stencil provided as a kit or unit.

FIG. 13 is a diagrammatical illustration of a combination of a skin-tightening composition in a container 1304 and a stencil 1306 provided as a kit or unit 1300. The container 1306 is any jar, tube, or other container suitable to contain a skin-tightening composition. The stencil 1306 is shown only as an example of an applicator, and is any suitable stamp or stencil disclosed herein. The container 1304 and applicator 1306 are held by molded plastic packaging 1302, for example. However, other suitable packaging is used to hold the applicator 1302 to the container 1304.

In an embodiment, a combination comprises a skin-tightening composition 108, 210 and an applicator 104, 202, 400, 500, 604, 700 configured to apply the skin-tightening composition in a discontinuous manner, wherein the applicator comprises an application surface having a plurality of first discontinuous subsurfaces 106, 204, 404, 503, 606, 706 separated by a continuous second subsurface 110, 206, 405, 502, 605, 708 where the plurality of discontinuous subsurfaces are arranged in a repeating pattern; and a skin-tightening composition.

In an embodiment, the first subsurfaces are open spaces 106, 503, 606 and the second subsurface forms ribs or strips 110, 502, 605 between the open spaces.

In an embodiment, the open spaces 106, 502, 605 have a non-isometric shape in the length and width dimensions.

In an embodiment, the open spaces 106, 502, 605 have diamond, square, rectangular, or any other polygon shape in the length and width dimension.

In an embodiment, the open spaces 106, 502, 605 have more than one shape.

In an embodiment, the open spaces 106, 502, 605 have more than one size.

In an embodiment, the skin-tightening composition 108, 210 is provided in a container 1202, 1212, and the applicator 104, 202, 400, 500, 604, 700 and skin-tightening composition are provided as a unit 1200, 1210.

In an embodiment, the skin-tightening composition 108, 210 is selected from the group consisting of: anionic copolymers based on methacrylic acid and methyl methacrylate in a random, block, or alternating configuration, organopolysiloxanes, silicone-urethane copolymers, ethylenically unsaturated polycarbosiloxanes, silicone-urethane copolymers and an elastomer, an elastomer, an adhesive polymer, and a filler, and wax microparticles In an embodiment, the combination comprises a stencil 104, 500, 604 including a material having a first and second major surface forming opposite sides of the material, wherein the first and second surfaces are separated by a thickness of the material with open spaces 106, 503, 606 in the material that traverse the material from the first major surface to the second major surface, wherein a majority of the open spaces have a similar shape to create a repeating pattern of open spaces along a length dimension and a width dimension of the material, and wherein the maximum average size of an open space in either a length dimension or width dimension is from 20 microns to 150 microns.

In an embodiment, the stencil 104, 500, 604 is a sheet or a mesh of filaments.

In an embodiment, the stencil 604 has an adhesive on one of the first or second major surfaces.

In an embodiment, the stencil 604 has a backing sheet 601 to which the stencil is adhered.

In an embodiment, the first subsurfaces are protrusions 204, 404, 706 and the second subsurface forms grooves 206, 405, 708 in between the first subsurfaces.

In an embodiment, outward facing surfaces of the distal ends of the protrusions 204, 404, 706 have a non-isometric shape in the length and width dimensions.

In an embodiment, outward facing surfaces of the distal ends of the protrusions 204, 404, 706 have a diamond, square, rectangular, or any other polygon shape in the length and width dimension.

In an embodiment, outward facing surfaces of the distal ends of the protrusions 204, 404, 706 include more than one shape of outward facing surface.

In an embodiment, outward facing surfaces of the distal ends of the protrusions 204, 404, 706 include more than one size of outward facing surfaces.

In an embodiment, outward facing surfaces of the distal ends of the protrusions 204, 404, 706 lie along a planar surface.

In an embodiment, outward facing surfaces of the distal ends of the protrusions 706 lie on a roller 704.

In an embodiment, outward facing surfaces of the distal ends of the protrusions 404 collectively lie on a convex surface.

In an embodiment, outward facing surfaces of the distal ends of the protrusions 404 lie on a convex surface curving upwards from a center in all dimensions.

In an embodiment, outward facing surfaces of the distal ends of the protrusions 204, 404, 706 are flat.

In an embodiment, the combination comprises a stamp 202, 400, 700 having protrusions 204, 404, 706 extending from at least one surface, wherein outward facing surfaces of the protrusions collectively form a surface for stamping, a majority of the outward facing surfaces of the distal ends of the protrusions have a similar shape to create a repeating pattern along a length dimension and a width dimension, and wherein the maximum average size of the outward facing surface area of the distal ends of the protrusions in either a length dimension or width dimension is from 20 microns to 150 microns.

In an embodiment, a method of applying a skin-tightening composition 108 comprises placing a stencil 104, 500, 604 on a skin area 102, wherein the stencil includes a material having a first and second major surface forming opposite sides of the material, wherein the first and second surfaces are separated by a thickness of the material with open spaces in the material that traverse the material from the first major surface to the second major surface, wherein a majority of the open spaces have a similar shape to create a repeating pattern of open spaces along a length dimension and a width dimension of the material, and wherein the maximum average size of an open space in either a length dimension or width dimension is from 20 microns to 150 microns; applying a skin-tightening composition to the stencil while on the skin area; and removing the stencil from the skin area that leaves a patterned skin-tightening composition on the skin area.

In an embodiment, a method of applying a skin-tightening composition 210, comprises providing a stamp 202, 400, 700 having protrusions 204, 404, 706 extending from at least one surface 206, 405, 708 wherein outward facing surfaces of the protrusions collectively form a surface for stamping, a majority of the outward facing surfaces of the distal ends of the protrusions have a similar shape to create a repeating pattern along a length dimension and a width dimension, and wherein the maximum average size of the outward facing surface area of the distal ends of the protrusions in either a length dimension or width dimension is from 20 microns to 150 microns; applying a skin-tightening composition 210 at least on the outward facing surfaces of the protrusions and bringing the skin-tightening composition on the stamp in contact with a skin area; and withdrawing the stamp and leaving a patterned skin-tightening composition on the skin area.

While illustrative embodiments have been illustrated and described, it will be appreciated that various changes can be made therein without departing from the spirit and scope of the invention.

The embodiments of the invention in which an exclusive property or privilege is claimed are defined as follows:

1. A combination comprising: a skin-tightening liquid composition and an applicator configured to apply the skin-tightening composition in a discontinuous manner, wherein the applicator comprises:
   a thin sheet of flexible material having two major surfaces, wherein the thin sheet is cut along a thickness into a plurality of first discontinuous subsurfaces separated by a continuous second subsurface, where the plurality of discontinuous subsurfaces are arranged in a repeating pattern;
   an adhesive on one of the two major surfaces;
   a removable backing sheet adhered to the adhesive, the backing sheet is configured to be removed while leaving the adhesive on the continuous second subsurface on the one of the two major surfaces, and cut material within the first discontinuous subsurfaces remains on the backing sheet; and
   wherein the skin-tightening liquid composition is configured to form a discontinuous skin-tightening film having a Young's modulus greater than 500 kPa, wherein the discontinuous skin-tightening film has greater flexibility than a continuous skin-tightening film of similar composition.

2. The combination of claim 1, wherein the first subsurfaces are open spaces and the second subsurface forms ribs or strips between the open spaces.

3. The combination of claim 2, wherein the open spaces have a non-isometric shape in a length and a width dimension.

4. The combination of claim 2, wherein the open spaces have diamond, square, rectangular, or any other polygon shape in a length and a width dimension.

5. The combination of claim 2, wherein the open spaces have more than one shape.

6. The combination of claim 2, wherein the open spaces have more than one size.

7. The combination of claim 1, wherein the skin-tightening liquid composition is provided in a container, and the applicator and skin-tightening liquid composition are provided as a unit.

8. The combination of claim 1, wherein the skin-tightening liquid composition is selected from the group consisting of:
   anionic copolymers based on methacrylic acid and methyl methacrylate in a random, block, or alternating configuration,
   organopolysiloxanes,
   silicone-urethane copolymers,
   ethylenically unsaturated polycarbosiloxanes,
   silicone-urethane copolymers and an elastomer,
   an elastomer, an adhesive polymer, and a filler, and
   wax microparticles.

9. The combination of claim 1, wherein the applicator is a stencil and the plurality of first discontinuous subsurfaces are open spaces in the material that traverse the material from the first major surface to the second major surface, wherein a majority of the open spaces have a similar shape to create a repeating pattern of open spaces along a length dimension and a width dimension of the material, and wherein a maximum average size of each of the open spaces in either a length dimension or width dimension is from 20 microns to 150 microns.

10. The combination of claim 9, wherein the stencil is a sheet or a mesh of filaments.

* * * * *